(12) United States Patent
Sinnott et al.

(10) Patent No.: US 9,662,105 B2
(45) Date of Patent: May 30, 2017

(54) SUTURE PASSER AND METHOD

(71) Applicant: Smith & Nephew, Inc., Memphis, TN (US)

(72) Inventors: M. Mary Sinnott, Logan, UT (US); T. Wade Fallin, Hyde Park, UT (US)

(73) Assignee: Smith & Nephew, Inc., Memphis, TN (US)

( * ) Notice: Subject to any disclaimer, the term of this patent is extended or adjusted under 35 U.S.C. 154(b) by 152 days.

(21) Appl. No.: 13/766,685

(22) Filed: Feb. 13, 2013

(65) Prior Publication Data

US 2013/0158570 A1     Jun. 20, 2013

Related U.S. Application Data

(63) Continuation-in-part of application No. 13/527,424, filed on Jun. 19, 2012.

(60) Provisional application No. 61/568,137, filed on Dec. 7, 2011, provisional application No. 61/505,992, filed on Jul. 8, 2011, provisional application No. 61/506,000, filed on Jul. 8, 2011, provisional application No. 61/506,004, filed on Jul. 8, 2011.

(51) Int. Cl.
*A61B 17/04* (2006.01)
*A61B 17/06* (2006.01)

(52) U.S. Cl.
CPC ...... *A61B 17/0491* (2013.01); *A61B 17/0482* (2013.01); *A61B 17/0483* (2013.01); *A61B 17/0469* (2013.01); *A61B 2017/0496* (2013.01); *A61B 2017/06042* (2013.01)

(58) Field of Classification Search
CPC .............. A61B 17/062; A61B 17/0491; A61B 17/0469; A61B 2017/0496; A61B 2017/0475; A61B 2017/0477; A61B 17/0482; A61B 17/0483; A61B 17/0485; D05B 1/00–1/26
USPC ........................................................ 606/147
See application file for complete search history.

(56) References Cited

U.S. PATENT DOCUMENTS

| | | |
|---|---|---|
| 919,138 A | 4/1909 | Drake |
| 1,037,864 A | 9/1912 | Carlson |
| 1,449,087 A | 3/1923 | Bugbee |
| 1,635,066 A | 7/1927 | Wells |
| 1,815,725 A | 7/1931 | Pilling et al. |
| 1,822,330 A | 9/1931 | Ainslie |

(Continued)

FOREIGN PATENT DOCUMENTS

| | | |
|---|---|---|
| CA | 2750377 A1 | 7/2010 |
| GB | 2475491 A | 5/2011 |

(Continued)

OTHER PUBLICATIONS

2008 Arthrex Inc., "*The Arthrex Scorpion*" 6 pages.

(Continued)

*Primary Examiner* — David C Eastwood
*Assistant Examiner* — Mikail Mannan
(74) *Attorney, Agent, or Firm* — Taft Stettinius & Hollister LLP

(57) ABSTRACT

Instruments and techniques to pass a suture are presented. The instruments and techniques are particularly useful where access to confined spaces and the ability to pass a suture through difficult to penetrate materials are needed. The instruments and techniques are particularly useful in surgery of the hands and feet.

19 Claims, 38 Drawing Sheets

(56) References Cited

U.S. PATENT DOCUMENTS

| | | |
|---|---|---|
| 1,856,721 A | 5/1932 | Nagelmann |
| 1,918,700 A | 7/1933 | Harris |
| 1,933,024 A | 10/1933 | Nagelmann |
| 1,981,651 A | 11/1934 | Logan |
| 2,240,330 A | 4/1941 | Flagg et al. |
| 2,269,963 A | 1/1942 | Wappler |
| 2,286,578 A | 6/1942 | Sauter |
| 2,301,500 A | 11/1942 | Anderson |
| 2,577,240 A | 12/1951 | Findley |
| 2,697,433 A | 12/1954 | Zehnder |
| 2,738,790 A | 3/1956 | Todt, Sr. et al. |
| 3,013,559 A | 12/1961 | Thomas |
| 3,090,386 A | 5/1963 | Curtis |
| 3,470,875 A | 10/1969 | Johnson |
| 3,638,653 A | 2/1972 | Berry |
| 3,840,017 A | 10/1974 | Violante |
| 3,842,840 A | 10/1974 | Schweizer |
| 3,946,740 A | 3/1976 | Bassett |
| 4,109,658 A | 8/1978 | Hughes |
| 4,164,225 A | 8/1979 | Johnson et al. |
| 4,172,458 A | 10/1979 | Pereyra |
| 4,224,947 A | 9/1980 | Fukuda |
| 4,345,601 A | 8/1982 | Fukuda |
| 4,373,530 A | 2/1983 | Kilejian |
| 4,406,237 A | 9/1983 | Eguchi et al. |
| 4,417,532 A | 11/1983 | Yasukata |
| 4,493,323 A | 1/1985 | Albright et al. |
| 4,596,249 A | 6/1986 | Freda et al. |
| 4,686,972 A | 8/1987 | Kurland |
| 4,739,751 A | 4/1988 | Sapega et al. |
| 4,781,182 A | 11/1988 | Purnell et al. |
| 4,823,780 A | 4/1989 | Odensten et al. |
| 4,836,205 A | 6/1989 | Barrett |
| 4,883,048 A | 11/1989 | Purnell et al. |
| 4,890,615 A | 1/1990 | Caspari et al. |
| 4,923,461 A | 5/1990 | Caspari et al. |
| 4,929,247 A | 5/1990 | Rayhack |
| 4,935,027 A | 6/1990 | Yoon |
| 4,957,498 A | 9/1990 | Caspari et al. |
| 4,964,861 A | 10/1990 | Agee et al. |
| 5,042,983 A | 8/1991 | Rayhack |
| 5,059,201 A | 10/1991 | Asnis |
| 5,100,418 A * | 3/1992 | Yoon et al. ............ 606/139 |
| 5,112,335 A | 5/1992 | Laboureau et al. |
| 5,112,337 A | 5/1992 | Paulos et al. |
| 5,176,685 A | 1/1993 | Rayhack |
| 5,217,471 A | 6/1993 | Burkhart |
| 5,222,977 A | 6/1993 | Esser |
| 5,281,237 A | 1/1994 | Gimpelson |
| 5,284,487 A * | 2/1994 | Hartmeister ............ 606/205 |
| 5,312,422 A | 5/1994 | Trott |
| 5,312,423 A | 5/1994 | Rosenbluth |
| 5,318,577 A | 6/1994 | Li |
| 5,336,229 A | 8/1994 | Noda |
| 5,397,325 A | 3/1995 | Della Badia et al. |
| 5,431,666 A | 7/1995 | Sauer et al. |
| 5,433,722 A | 7/1995 | Sharpe et al. |
| 5,439,467 A | 8/1995 | Benderev et al. |
| 5,454,823 A | 10/1995 | Richardson et al. |
| 5,462,562 A | 10/1995 | Elkus |
| 5,474,565 A | 12/1995 | Trott |
| 5,499,991 A | 3/1996 | Garman et al. |
| 5,520,693 A | 5/1996 | McGuire et al. |
| 5,522,820 A | 6/1996 | Caspari et al. |
| 5,544,664 A | 8/1996 | Benderev et al. |
| 5,562,686 A | 10/1996 | Sauer et al. |
| 5,571,119 A | 11/1996 | Atala |
| 5,573,542 A | 11/1996 | Stevens |
| 5,575,801 A | 11/1996 | Habermeyer et al. |
| 5,618,290 A | 4/1997 | Toy et al. |
| 5,632,752 A | 5/1997 | Buelna |
| 5,645,552 A | 7/1997 | Sherts |
| 5,662,663 A | 9/1997 | Shallman |
| 5,662,664 A | 9/1997 | Gordon et al. |
| 5,665,096 A | 9/1997 | Yoon |
| 5,690,653 A | 11/1997 | Richardson et al. |
| 5,713,908 A | 2/1998 | Jameel et al. |
| 5,713,910 A | 2/1998 | Gordon et al. |
| 5,730,747 A | 3/1998 | Ek et al. |
| 5,741,277 A | 4/1998 | Gordon et al. |
| 5,741,278 A | 4/1998 | Stevens |
| 5,741,279 A | 4/1998 | Gordon et al. |
| 5,741,281 A | 4/1998 | Martin |
| 5,766,186 A | 6/1998 | Faraz et al. |
| 5,776,150 A | 7/1998 | Nolan et al. |
| 5,792,153 A | 8/1998 | Swain et al. |
| 5,797,927 A | 8/1998 | Yoon |
| 5,860,992 A | 1/1999 | Daniel et al. |
| 5,871,488 A | 2/1999 | Tovey et al. |
| 5,902,311 A | 5/1999 | Andreas et al. |
| 5,904,692 A | 5/1999 | Steckel et al. |
| 5,908,426 A | 6/1999 | Pierce |
| 5,919,199 A | 7/1999 | Mers Kelly et al. |
| 5,921,994 A | 7/1999 | Andreas et al. |
| 5,928,252 A | 7/1999 | Steadman et al. |
| 5,947,982 A | 9/1999 | Duran |
| 5,968,050 A | 10/1999 | Torrie |
| 5,980,538 A | 11/1999 | Fuchs et al. |
| 5,984,933 A | 11/1999 | Yoon |
| 6,007,535 A | 12/1999 | Rayhack et al. |
| 6,022,360 A | 2/2000 | Reimels et al. |
| 6,036,699 A | 3/2000 | Andreas et al. |
| 6,051,006 A | 4/2000 | Shluzas et al. |
| 6,071,289 A | 6/2000 | Stefanchik et al. |
| 6,074,403 A | 6/2000 | Nord |
| 6,096,051 A | 8/2000 | Kortenbach et al. |
| 6,136,010 A | 10/2000 | Modesitt et al. |
| 6,143,004 A | 11/2000 | Davis et al. |
| 6,156,039 A | 12/2000 | Thal |
| 6,187,011 B1 | 2/2001 | Torrie |
| 6,197,035 B1 | 3/2001 | Loubens et al. |
| 6,217,592 B1 | 4/2001 | Freda et al. |
| 6,270,503 B1 | 8/2001 | Schmieding |
| 6,296,659 B1 | 10/2001 | Foerster |
| 6,332,889 B1 | 12/2001 | Sancoff et al. |
| 6,475,135 B1 | 11/2002 | Levy |
| 6,511,487 B1 | 1/2003 | Oren et al. |
| 6,533,795 B1 | 3/2003 | Tran et al. |
| 6,533,796 B1 | 3/2003 | Sauer et al. |
| 6,551,330 B1 | 4/2003 | Bain et al. |
| 6,582,453 B1 | 6/2003 | Tran et al. |
| 6,585,730 B1 | 7/2003 | Foerster |
| 6,605,096 B1 | 8/2003 | Ritchart |
| 6,723,107 B1 | 4/2004 | Skiba et al. |
| 6,725,082 B2 | 4/2004 | Sati et al. |
| 6,700,076 B2 | 8/2004 | Foerster |
| 6,770,084 B1 | 8/2004 | Bain et al. |
| 6,802,807 B2 | 10/2004 | Anderson et al. |
| 6,855,157 B2 | 2/2005 | Foerster et al. |
| 6,878,150 B1 | 4/2005 | McGuire et al. |
| 6,893,448 B2 | 5/2005 | O'Queen et al. |
| 6,896,686 B2 | 5/2005 | Weber |
| 6,911,034 B2 | 6/2005 | Nobles et al. |
| 6,936,054 B2 | 8/2005 | Chu |
| 6,984,237 B2 | 1/2006 | Hatch et al. |
| 6,997,932 B2 | 2/2006 | Dreyfuss et al. |
| 7,025,770 B2 | 4/2006 | McGuire et al. |
| 7,083,638 B2 | 8/2006 | Foerster |
| 7,090,686 B2 | 8/2006 | Nobles et al. |
| 7,112,208 B2 | 9/2006 | Morris et al. |
| 7,118,583 B2 | 10/2006 | O'Quinn et al. |
| 7,122,040 B2 | 10/2006 | Hill |
| 7,198,631 B2 | 4/2007 | Kanner et al. |
| 7,232,448 B2 | 6/2007 | Battles et al. |
| 7,285,124 B2 | 10/2007 | Foerster |
| 7,297,145 B2 | 11/2007 | Woloszko et al. |
| 7,329,264 B2 | 2/2008 | Merves |
| 7,377,926 B2 | 5/2008 | Topper et al. |
| 7,449,024 B2 | 11/2008 | Stafford |
| 7,544,199 B2 | 6/2009 | Bain et al. |
| 7,572,265 B2 | 8/2009 | Stone et al. |
| 7,575,578 B2 | 8/2009 | Wetzler et al. |
| 7,585,305 B2 | 9/2009 | Dreyfuss |
| 7,608,084 B2 | 10/2009 | Oren et al. |

(56) References Cited

U.S. PATENT DOCUMENTS

| | | |
|---|---|---|
| 7,695,494 B2 | 4/2010 | Foerster |
| 7,717,912 B2 | 5/2010 | Woloszko et al. |
| 7,722,630 B1 | 5/2010 | Stone et al. |
| 7,727,256 B2 | 6/2010 | McGregor |
| 7,758,597 B1 | 7/2010 | Tran et al. |
| 7,771,438 B2 | 8/2010 | Dreyfuss et al. |
| 7,815,654 B2 | 10/2010 | Chu |
| 7,879,046 B2 | 2/2011 | Weinert et al. |
| 7,879,048 B2 | 2/2011 | Bain et al. |
| 7,883,519 B2 | 2/2011 | Oren et al. |
| 7,922,744 B2 | 4/2011 | Morris et al. |
| 7,963,972 B2 | 6/2011 | Foerster et al. |
| 7,972,344 B2 | 7/2011 | Murray et al. |
| 8,110,000 B2 | 2/2012 | Collins |
| 8,147,505 B2 | 4/2012 | Delli-Santi |
| 8,282,656 B2 | 10/2012 | Hart |
| 8,469,974 B2 | 6/2013 | Skinlo |
| 8,545,521 B2 | 10/2013 | McClurg |
| 8,647,354 B2 | 2/2014 | Domingo |
| 2001/0037119 A1 | 11/2001 | Schmieding |
| 2002/0147456 A1 | 10/2002 | Diduch et al. |
| 2002/0173800 A1 | 11/2002 | Dreyfuss et al. |
| 2003/0078599 A1* | 4/2003 | O'Quinn et al. ............ 606/144 |
| 2003/0078600 A1 | 4/2003 | O'Quinn et al. |
| 2003/0195528 A1 | 10/2003 | Ritchart |
| 2003/0216742 A1 | 11/2003 | Wetzler et al. |
| 2003/0220659 A1 | 11/2003 | Schmieding et al. |
| 2003/0233106 A1 | 12/2003 | Dreyfuss |
| 2004/0010273 A1 | 1/2004 | Diduch et al. |
| 2004/0015177 A1 | 1/2004 | Chu |
| 2004/0138682 A1 | 7/2004 | Onuki et al. |
| 2004/0249394 A1 | 12/2004 | Morris et al. |
| 2005/0165419 A1 | 7/2005 | Sauer et al. |
| 2005/0240226 A1 | 10/2005 | Foerster et al. |
| 2006/0052801 A1 | 3/2006 | Dreyfuss et al. |
| 2006/0241658 A1 | 10/2006 | Cerundolo |
| 2006/0271060 A1 | 11/2006 | Gordon |
| 2007/0060953 A1 | 3/2007 | Morris et al. |
| 2007/0088362 A1 | 4/2007 | Bonutti et al. |
| 2007/0118150 A1 | 5/2007 | Weber |
| 2007/0149986 A1 | 6/2007 | Morris et al. |
| 2007/0179524 A1 | 8/2007 | Weber et al. |
| 2007/0233128 A1 | 10/2007 | Schmieding et al. |
| 2008/0015594 A1 | 1/2008 | Ritchart et al. |
| 2008/0097482 A1 | 4/2008 | Bain et al. |
| 2009/0036905 A1 | 2/2009 | Schmieding |
| 2009/0062816 A1 | 3/2009 | Weber |
| 2009/0062819 A1 | 3/2009 | Burkhart et al. |
| 2009/0105751 A1* | 4/2009 | Zentgraf ............... 606/206 |
| 2009/0131956 A1 | 5/2009 | Dewey et al. |
| 2009/0222040 A1 | 9/2009 | Foerster |
| 2009/0222041 A1 | 9/2009 | Foerster |
| 2009/0254126 A1 | 10/2009 | Orbay et al. |
| 2009/0318965 A1 | 12/2009 | Burkhart |
| 2010/0057216 A1 | 3/2010 | Gannoe et al. |
| 2010/0137889 A1 | 6/2010 | Oren et al. |
| 2010/0152752 A1 | 6/2010 | Denove et al. |
| 2010/0191283 A1 | 7/2010 | Foerster et al. |
| 2010/0211082 A1 | 8/2010 | Sauer |
| 2010/0211083 A1 | 8/2010 | Sauer |
| 2010/0249806 A1 | 9/2010 | Oren et al. |
| 2010/0268256 A1 | 10/2010 | Dreyfuss et al. |
| 2010/0324563 A1 | 12/2010 | Green, II et al. |
| 2010/0331623 A1 | 12/2010 | Sauer |
| 2011/0009867 A1 | 1/2011 | Oren et al. |
| 2011/0066165 A1 | 3/2011 | Skinlo et al. |
| 2011/0144647 A1 | 6/2011 | Appenzeller et al. |
| 2011/0144666 A1 | 6/2011 | Egle |
| 2011/0208198 A1 | 8/2011 | Anderson et al. |
| 2011/0276064 A1 | 11/2011 | Henrichsen |
| 2012/0143220 A1 | 6/2012 | Morgan |
| 2012/0283750 A1 | 11/2012 | Saliman |
| 2012/0303046 A1 | 11/2012 | Stone |

FOREIGN PATENT DOCUMENTS

| | | |
|---|---|---|
| JP | 2014528768 A | 10/2014 |
| WO | 9106247 A1 | 5/1991 |
| WO | WO 03/007799 A2 | 1/2003 |
| WO | WO 2004/002324 A1 | 1/2004 |
| WO | 2008043380 A1 | 4/2008 |
| WO | 2008076559 A1 | 6/2008 |

OTHER PUBLICATIONS

Coughlin, et al. "Second MTP Joint Instability: Grading of the Deformity and Description of Surgical Repair of Capsular Insufficiency" The Physician and Sportmedicine, Sep. 3, 2011, 39(3):132-141.

Blitz, et al. "Plantar Plate Repair of the Second Metatarsophalangeal Joint: Technique and Tips" Journal of Foot & Ankle Surgery, 2004 43(4):266-270.

Fleming and Camasta, "Plantar Plate Dysfunction" Chapter 4, (2002) pp. 22-28, http://www.podiatryinstitute.com/pdfs/Update_2002/2002_04.pdf.

Gregg et al., "Plantar Plate Repair and Weil Osteotomy for Metatarsophalangeal Joint Instability" Foot and Ankle Surgery, (2007) 13:116-121.

Nery et al., "Lesser Metatarsophalangeal Joint Instability: Prospective Evaluation and Repair of Plantar Plate and Capsular Insufficiency" Foot and Ankle International, Apr. 2012 33(4):301-311.

International Search Report; International Searching Authority; International PCT Application No. PCT/US2012/045584; Jan. 31, 2013; 3 pages.

Written Opinion; International Searching Authority; International PCT Application No. PCT/US2012/045584; Jan. 31, 2013; 4 pages.

International Preliminary Report on Patentability; The International Bureau of WIPO; International PCT Application No. PCT/US2012/045584; Jan. 14, 2014; 5 pages.

Supplementary Partial European Search Report; European Patent Office; European Patent Application No. 12810809.9; Apr. 1, 2015; 6 pages.

European Patent Office, Supplementary Partial European Search Report, dated Apr. 1, 2015, 6 pages.

Japanese Notice of Reasons for Rejection; Japanese Patent Office; Japanese Patent Application No. 2014-519300; Jun. 20, 2016; 11 pages.

Chinese Search Report; Chinese Patent Office; Chinese Patent Application No. 201280043613.2; Oct. 20, 2016; 4 pages.

Chinese Decision of Rejection; Chinese Patent Office; Chinese Patent Application No. 201280043613.2; Nov. 1, 2016; 15 pages.

Extended European Search Report; European Patent Office; European Application No. 12810809.9; Feb. 15, 2016; 21 pages.

Australian Patent Examination Report; Australian Patent Office; Australian Patent Application No. 2012282919; Apr. 14, 2016; 3 pages.

Japanese Notice of Reasons for Rejection; Japanese Patent Office; Japanese Patent Application No. 2014-519300; Mar. 27, 2017; 5 pages.

\* cited by examiner

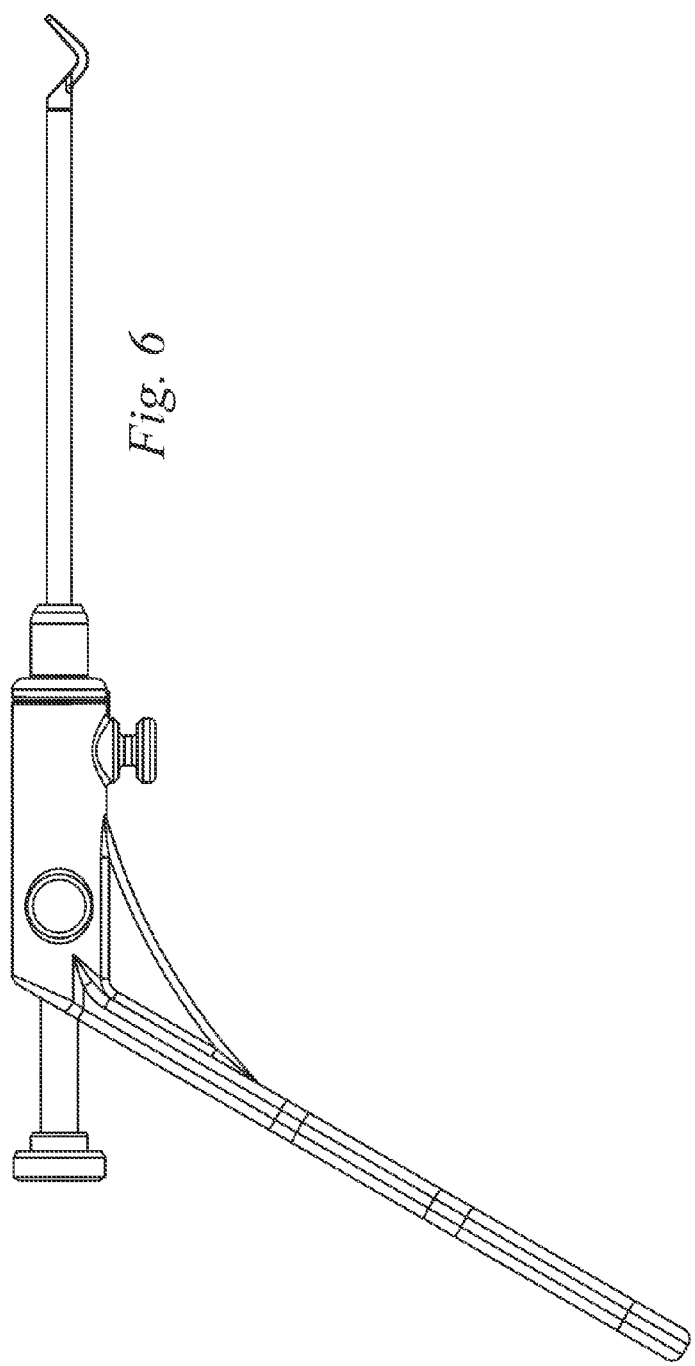
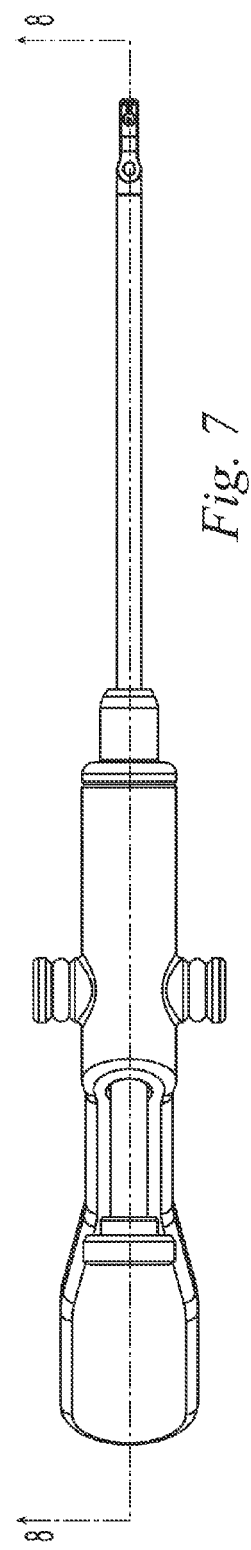
Fig. 6
Fig. 7

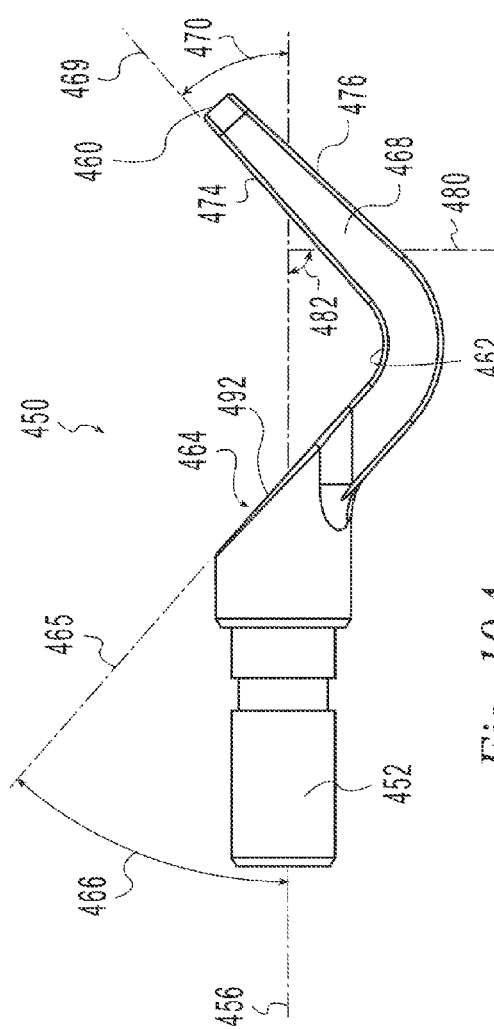
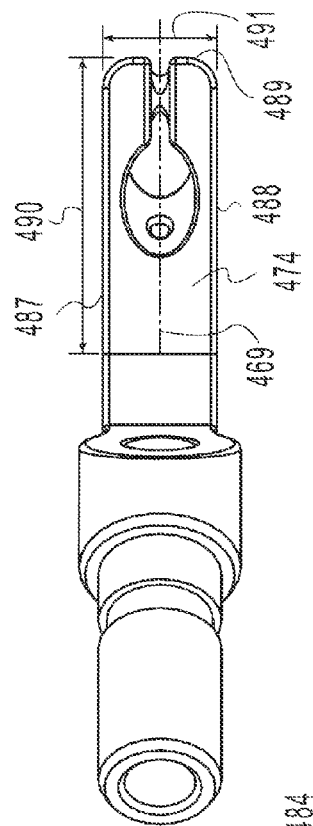
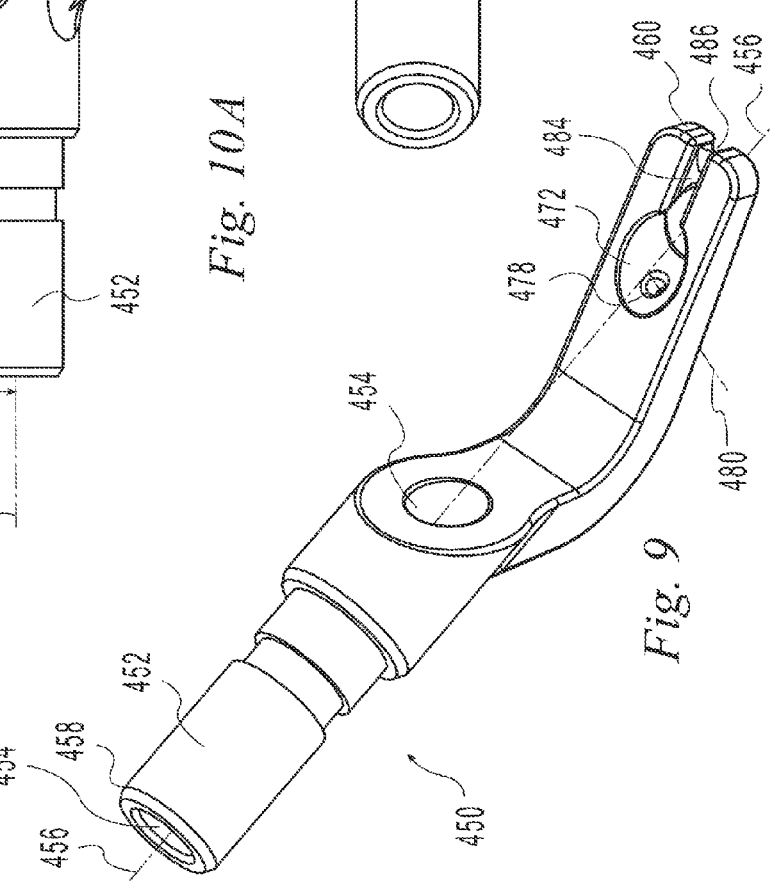
Fig. 10A
Fig. 10B
Fig. 9

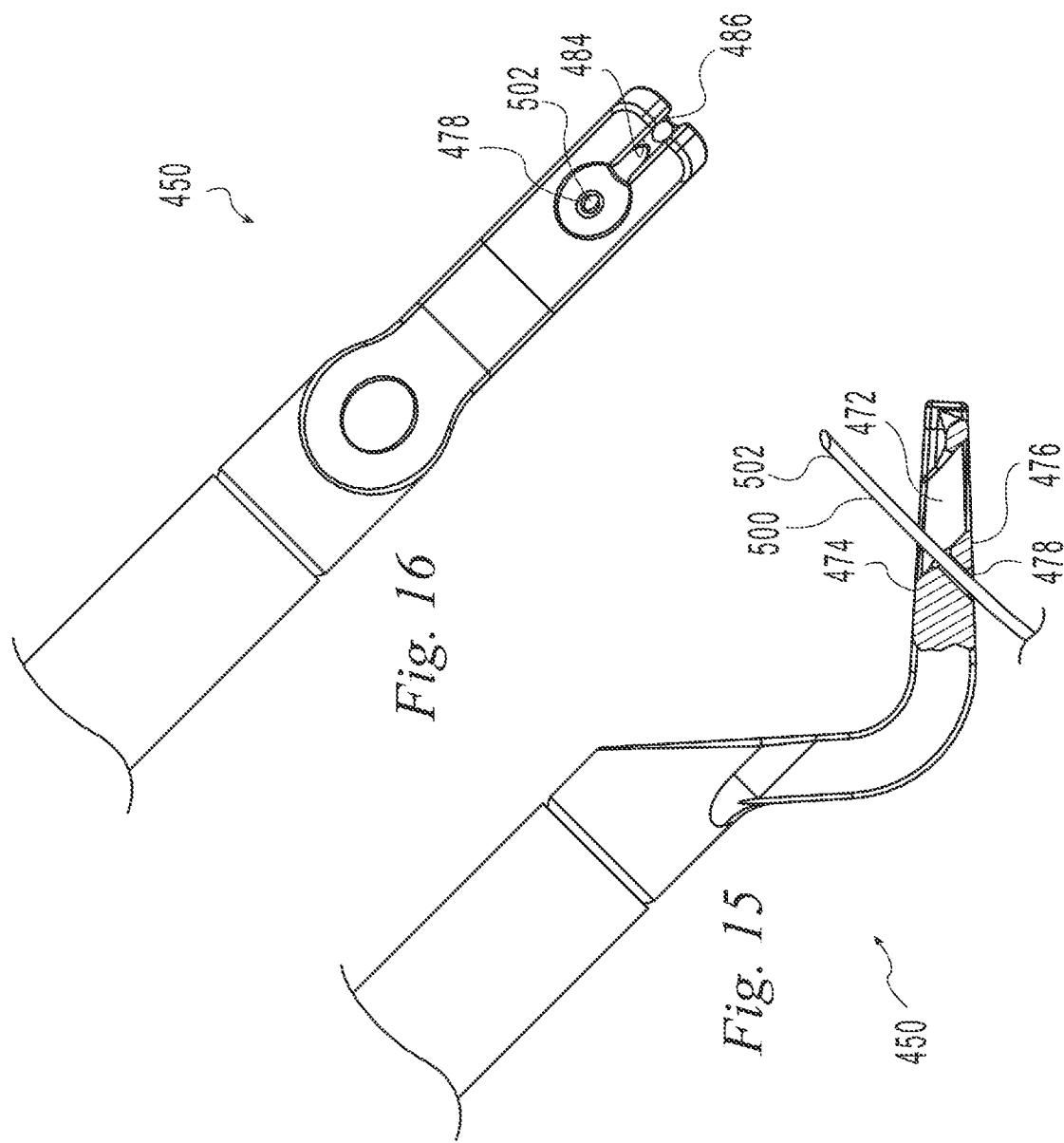

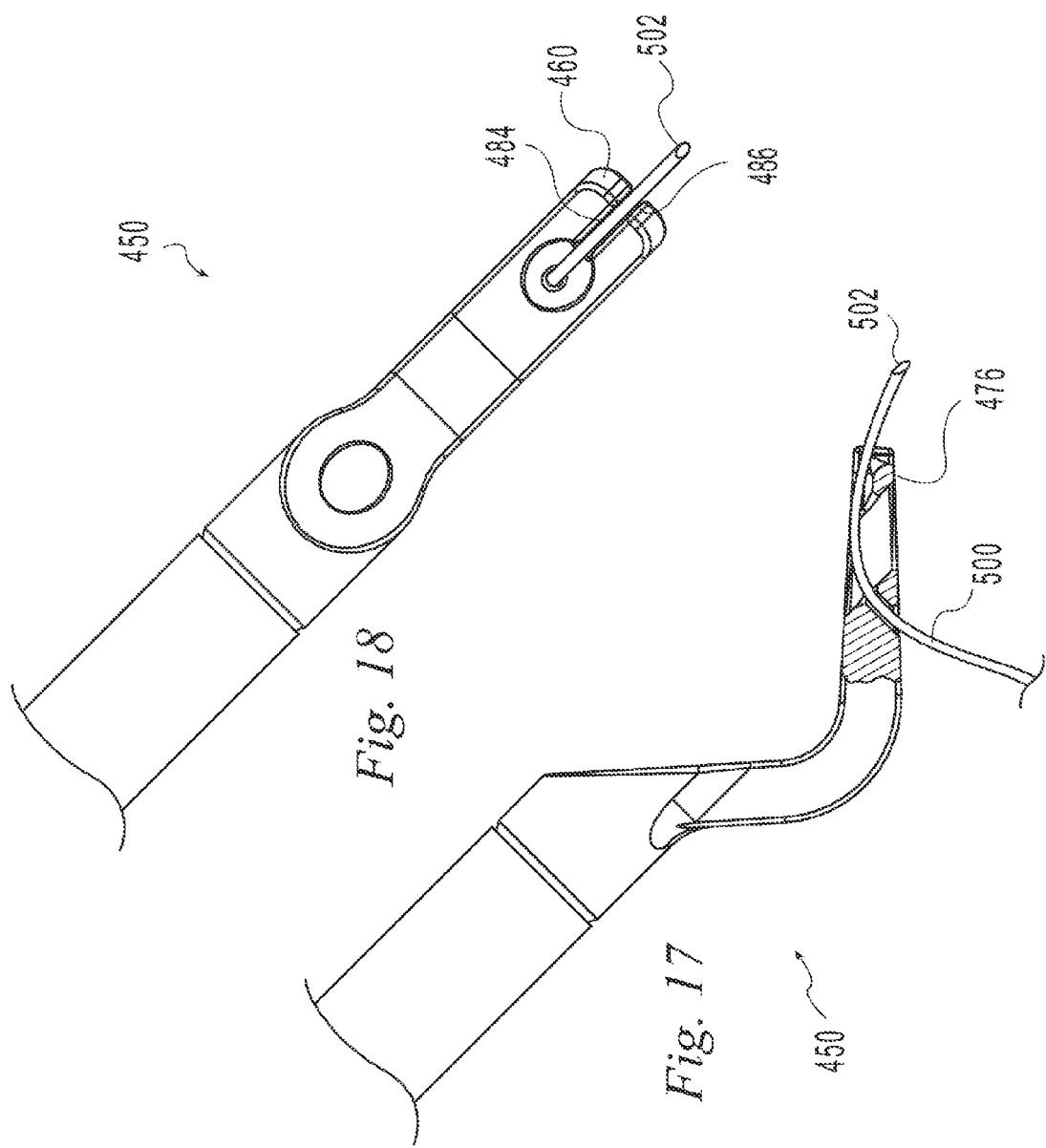

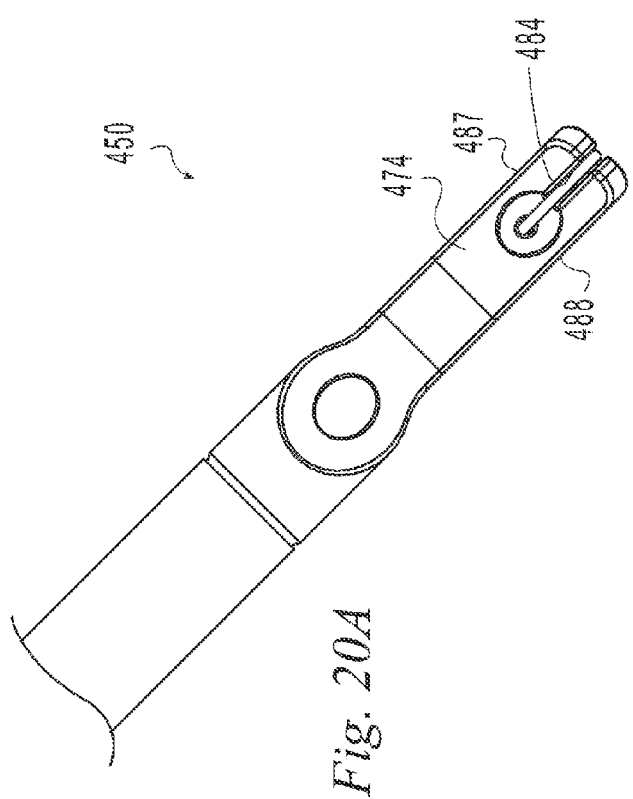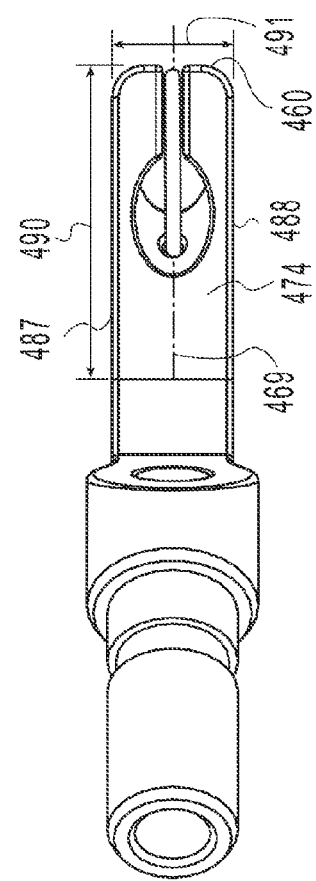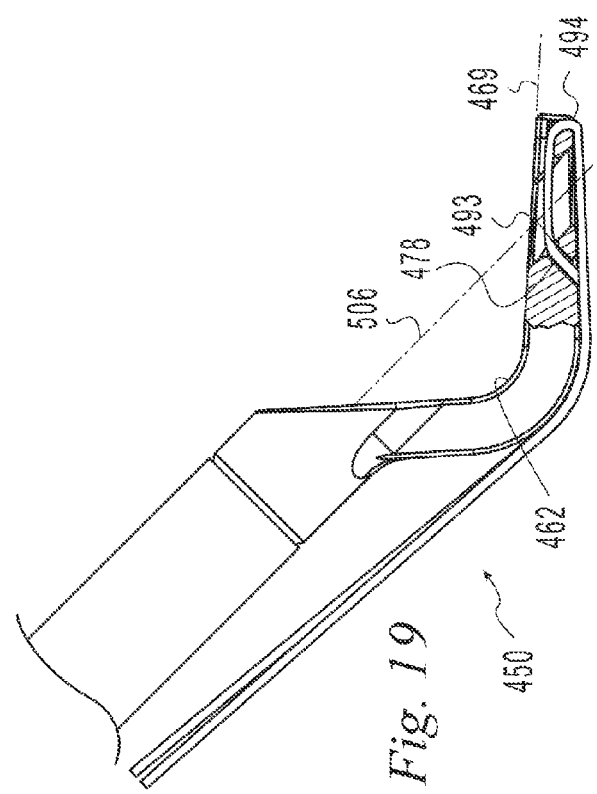

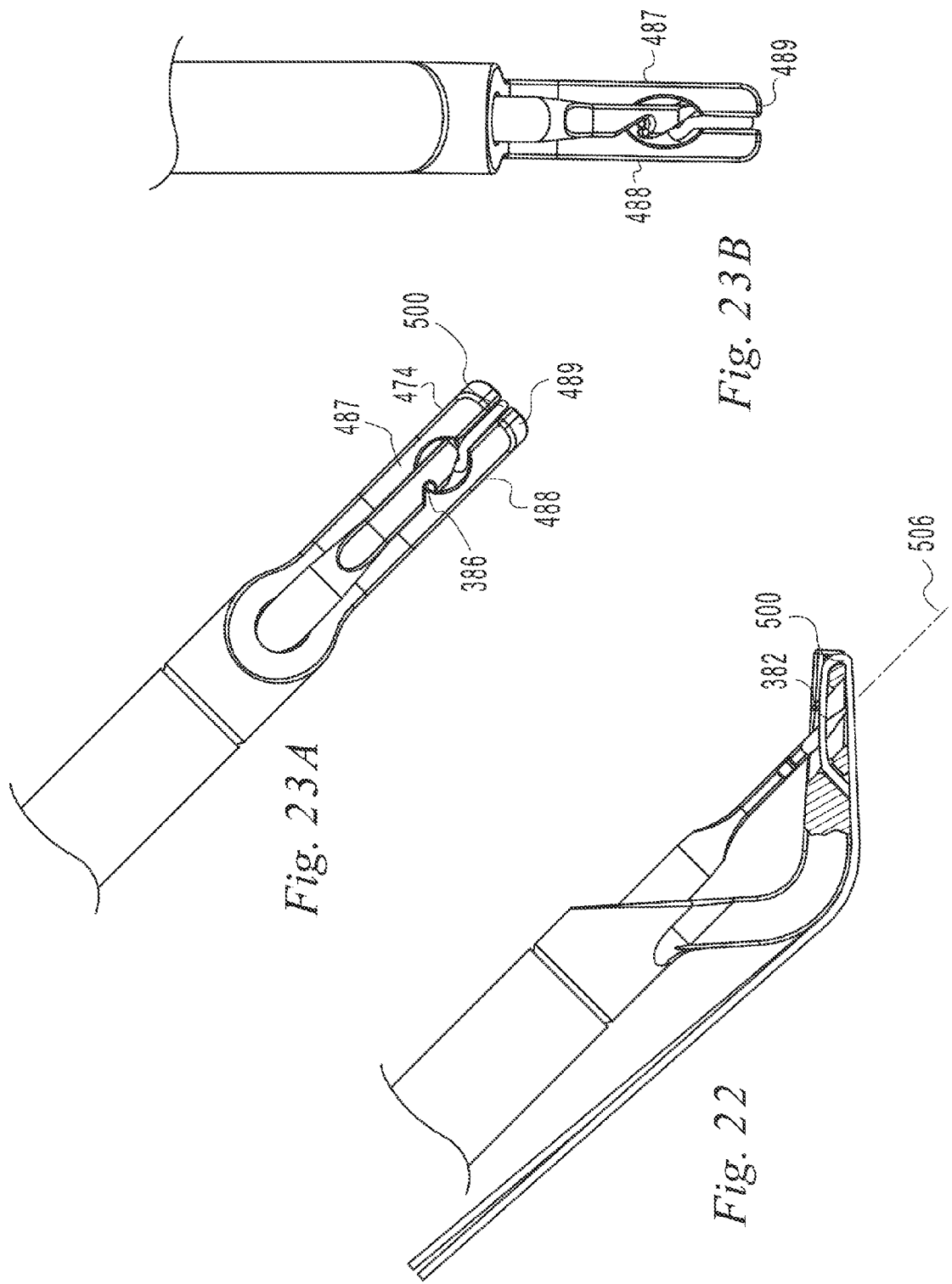

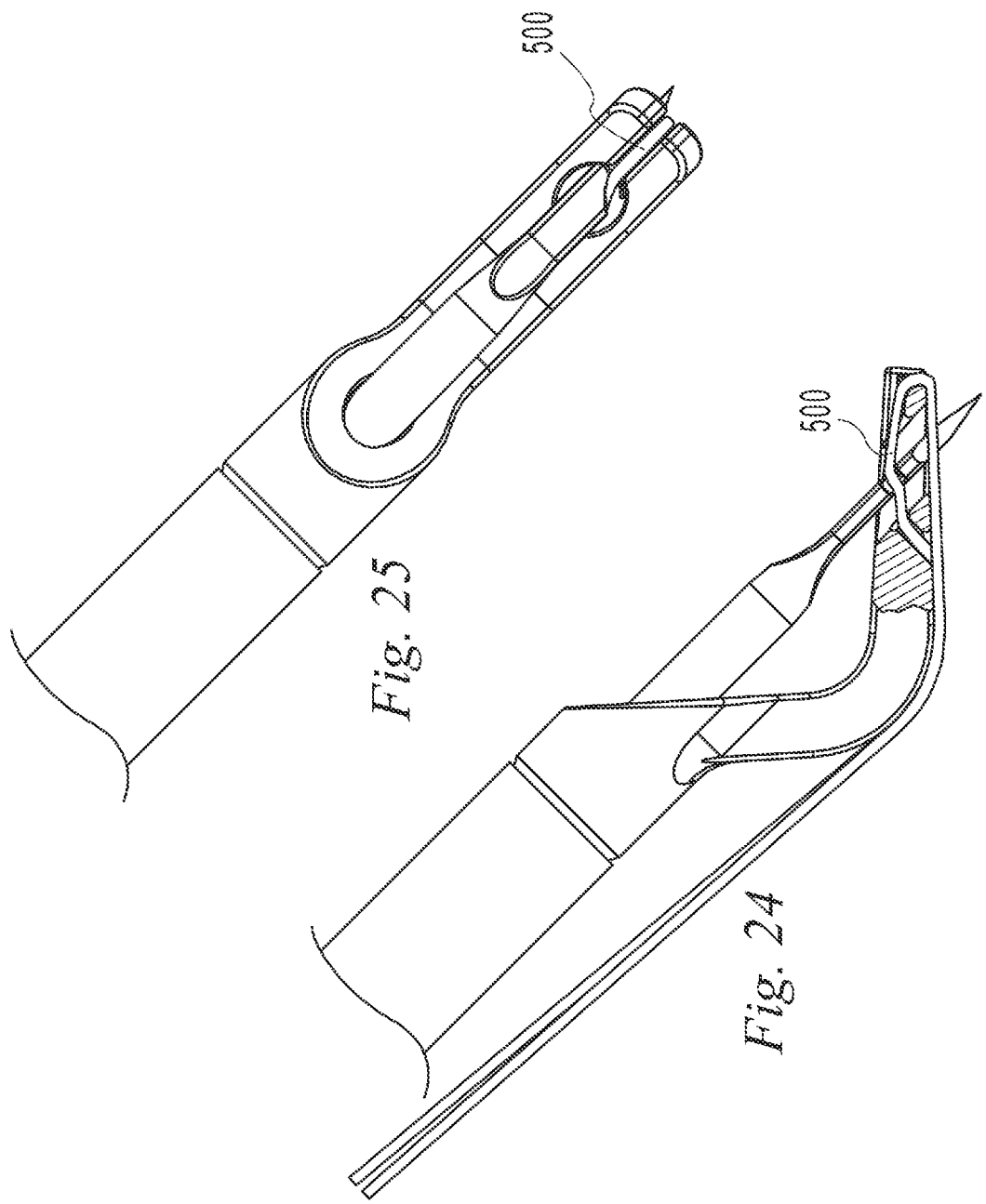

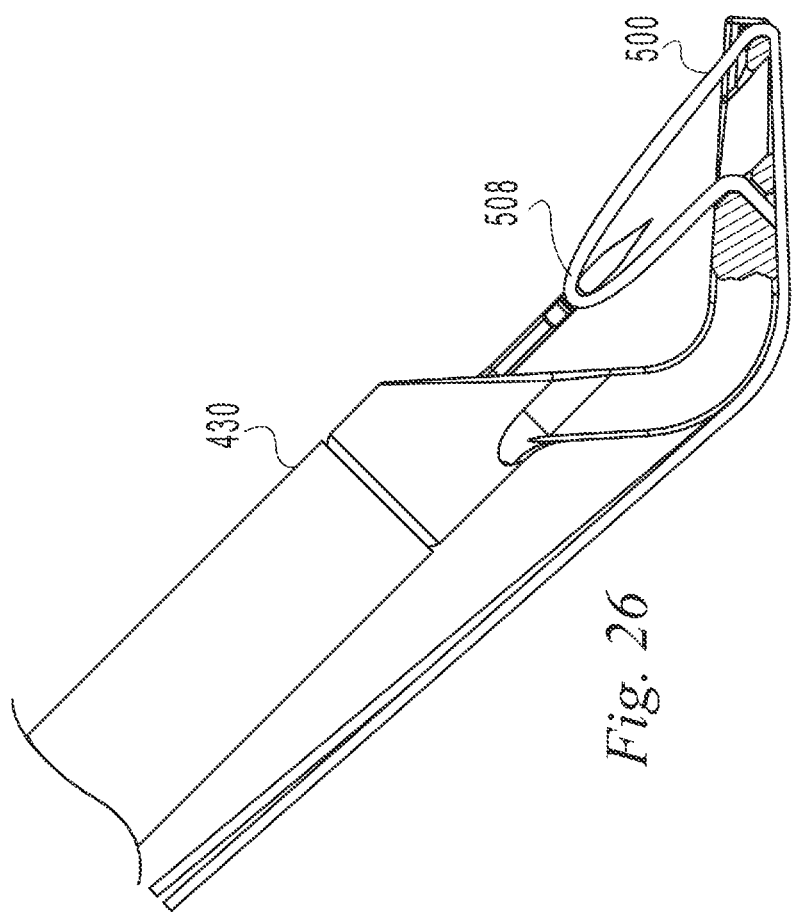

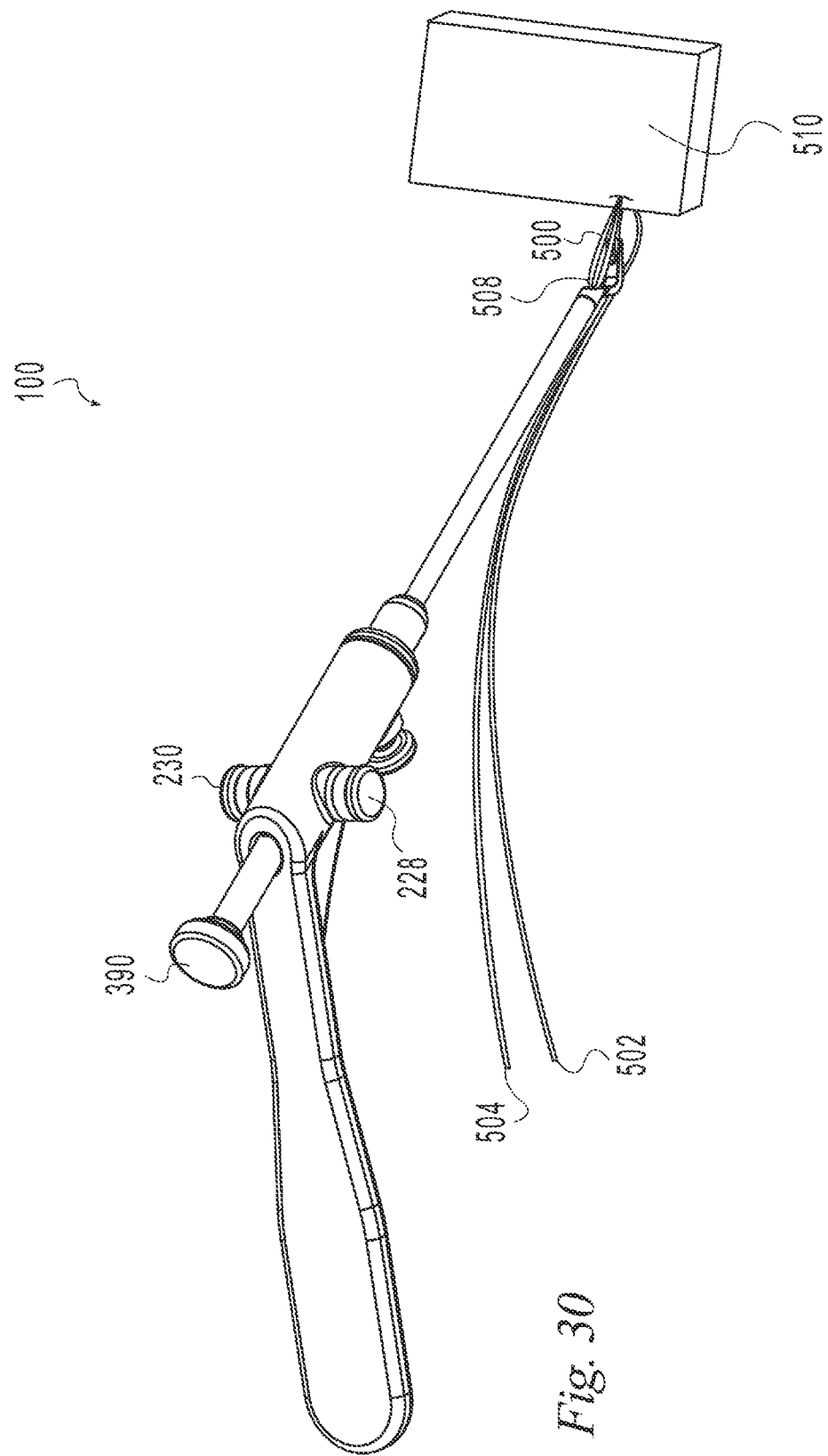

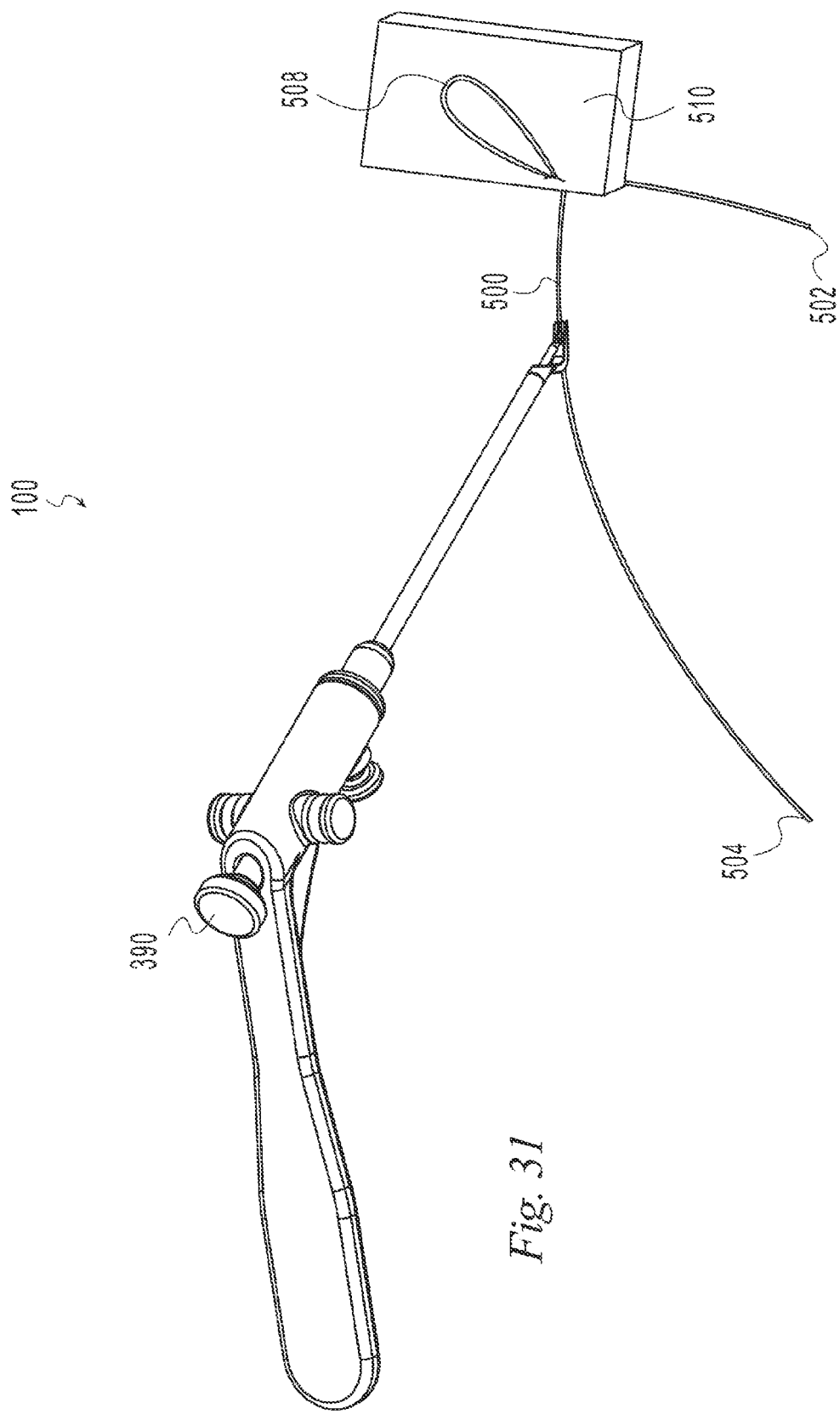

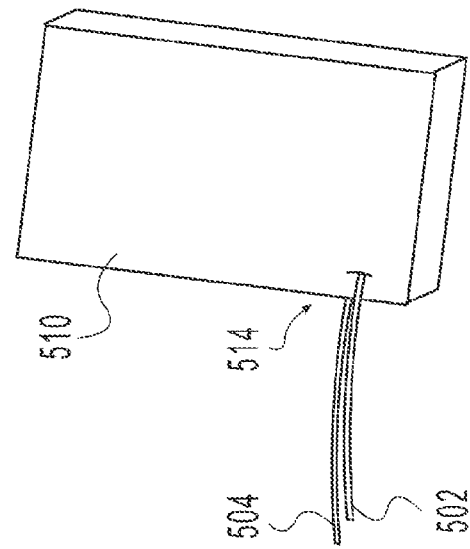
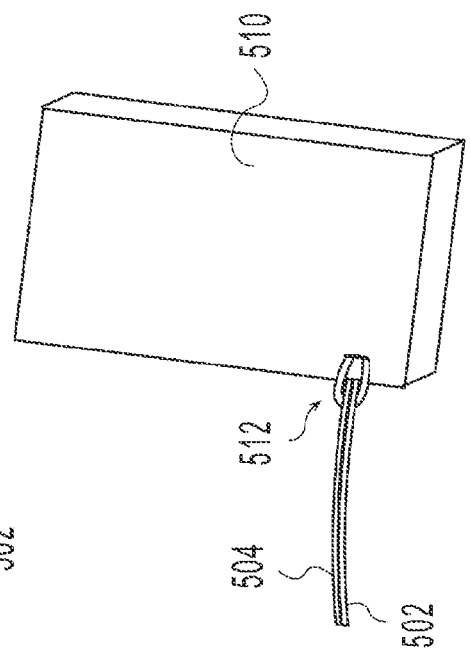
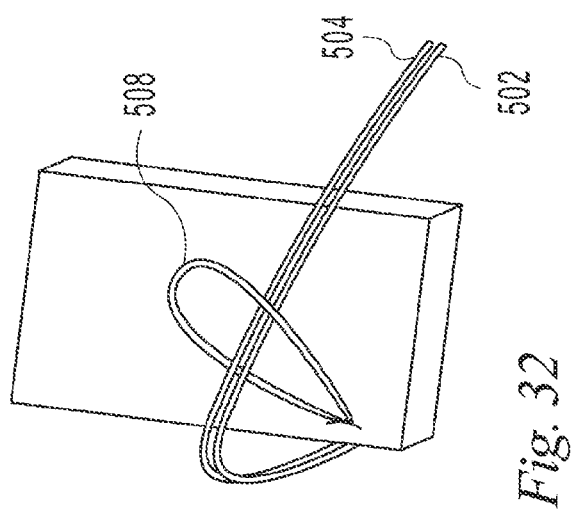

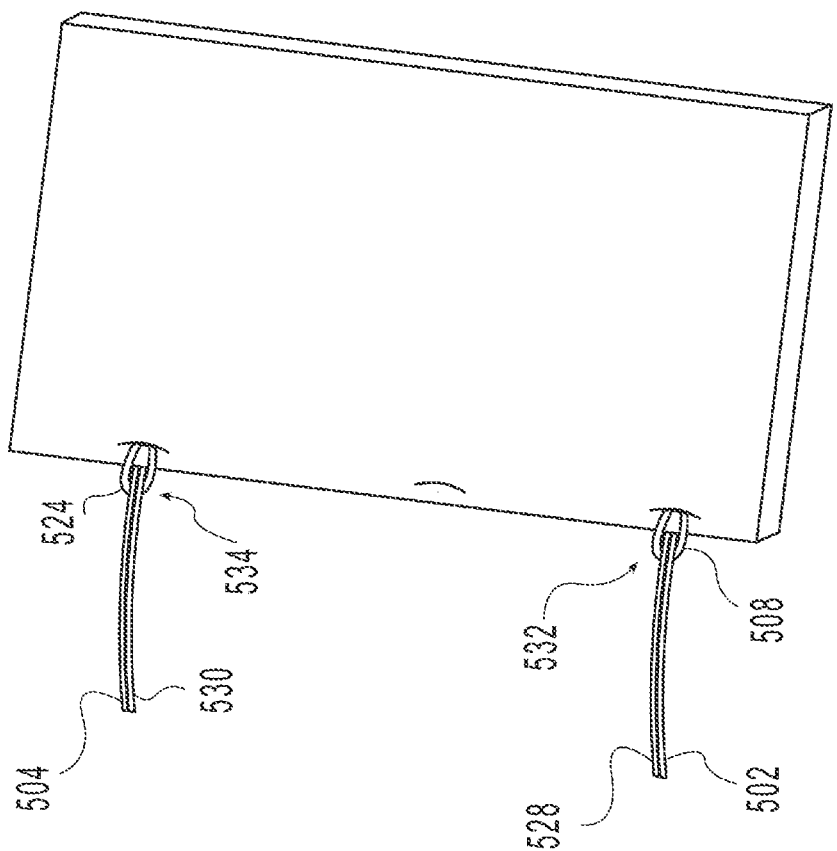

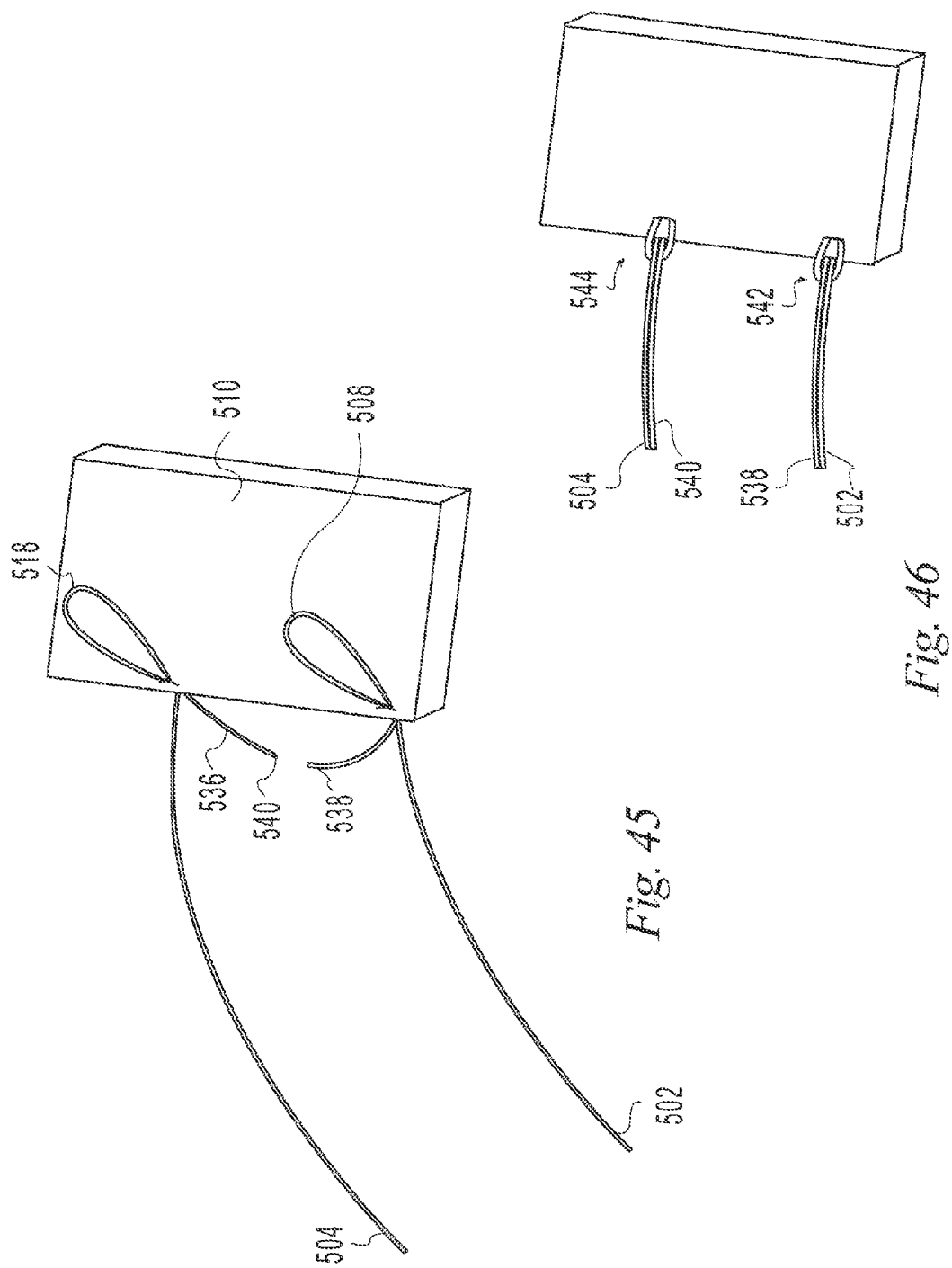

SUTURE PASSER AND METHOD

CROSS-REFERENCE TO RELATED APPLICATIONS

This application is a continuation-in-part of U.S. patent application Ser. No. 13/527,424, filed Jun. 19, 2012, which claims the benefit of U.S. Provisional Application No. 61/568,137, filed Dec. 7, 2011, U.S. Provisional Application No. 61/505,992, filed Jul. 8, 2011, U.S. Provisional Application No. 61/506,000, filed Jul. 8, 2011, U.S. Provisional Application No. 61/506,004, filed Jul. 8, 2011, all of which are herein incorporated by reference.

FIELD OF THE INVENTION

The invention relates to devices and methods to pass a suture and, in particular, to suturing material such as, for example, soft tissue in reconstructive surgery of a joint such as for example of the foot or hand.

BACKGROUND

Various conditions affecting a patient may require surgical intervention involving passing a suture for example to repair a tear, repair an incision, pass grafts, attach grafts, and anchor implants. Various suture passers have been proposed. There is a need for an improved suture passer able to access confined spaces and able to pass a suture through difficult to penetrate materials such as tough connective tissues.

SUMMARY

The present invention provides a suture passer and method to pass a suture through material during a surgical intervention.

In one aspect of the invention a suture passer includes a housing defining a linear motion axis extending proximally to distally and a needle mounted for translation along the motion axis between a first proximal position and a second distal position. The suture passer may include a foot mounted to the housing and having an opening in a proximal facing surface to receive the needle in the second position.

BRIEF DESCRIPTION OF THE DRAWINGS

Various examples of the present invention will be discussed with reference to the appended drawings. These drawings depict only illustrative examples of the invention and are not to be considered limiting of its scope.

FIG. 6 is a side elevation view of the suture passer of FIG. 1;

FIG. 7 is a top plan view of the suture passer of FIG. 1;

FIG. 9 is a perspective view of a component of the suture passer of FIG. 1;

FIG. 10A is a side elevation view of the component of FIG. 9;

FIG. 10B is a plan view normal to the surface 474 of FIG. 10A;

FIG. 15 is a partially sectioned side elevation view of the distal end of the suture passer of FIG. 1 illustrating a suture being loaded on the suture passer;

FIG. 16 is a top plan view of the distal end of the suture passer of FIG. 1 illustrating a suture being loaded on the suture passer;

FIG. 17 is a partially sectioned side elevation view of the distal end of the suture passer of FIG. 1 illustrating a suture being loaded on the suture passer;

FIG. 18 is a top plan view of the distal end of the suture passer of FIG. 1 illustrating a suture being loaded on the suture passer;

FIG. 19 is a partially sectioned side elevation view of the distal end of the suture passer of FIG. 1 illustrating a suture being loaded on the suture passer;

FIG. 20A is a top plan view of the distal end of the suture passer of FIG. 1 illustrating a suture being loaded on the suture passer;

FIG. 20B is a plan view normal to surface 474 of FIG. 20A;

FIG. 22 is a partially sectioned side elevation view of the distal end of the suture passer of FIG. 1 illustrating the operation of the suture passer;

FIG. 23A is a top plan view of the distal end of the suture passer of FIG. 1 illustrating the operation of the suture passer;

FIG. 23B is a plan view normal to surface 474 of FIG. 23A;

FIG. 24 is a partially sectioned side elevation view of the distal end of the suture passer of FIG. 1 illustrating the operation of the suture passer;

FIG. 25 is a top plan view of the distal end of the suture passer of FIG. 1 illustrating the operation of the suture passer;

FIG. 26 is a partially sectioned side elevation view of the distal end of the suture passer of FIG. 1 illustrating the operation of the suture passer;

FIGS. 28-46 are perspective views illustrating the suture passer of FIG. 1 in use to pass sutures through a material to create a variety of stitches;

DESCRIPTION OF THE ILLUSTRATIVE EXAMPLES

Figure 1:
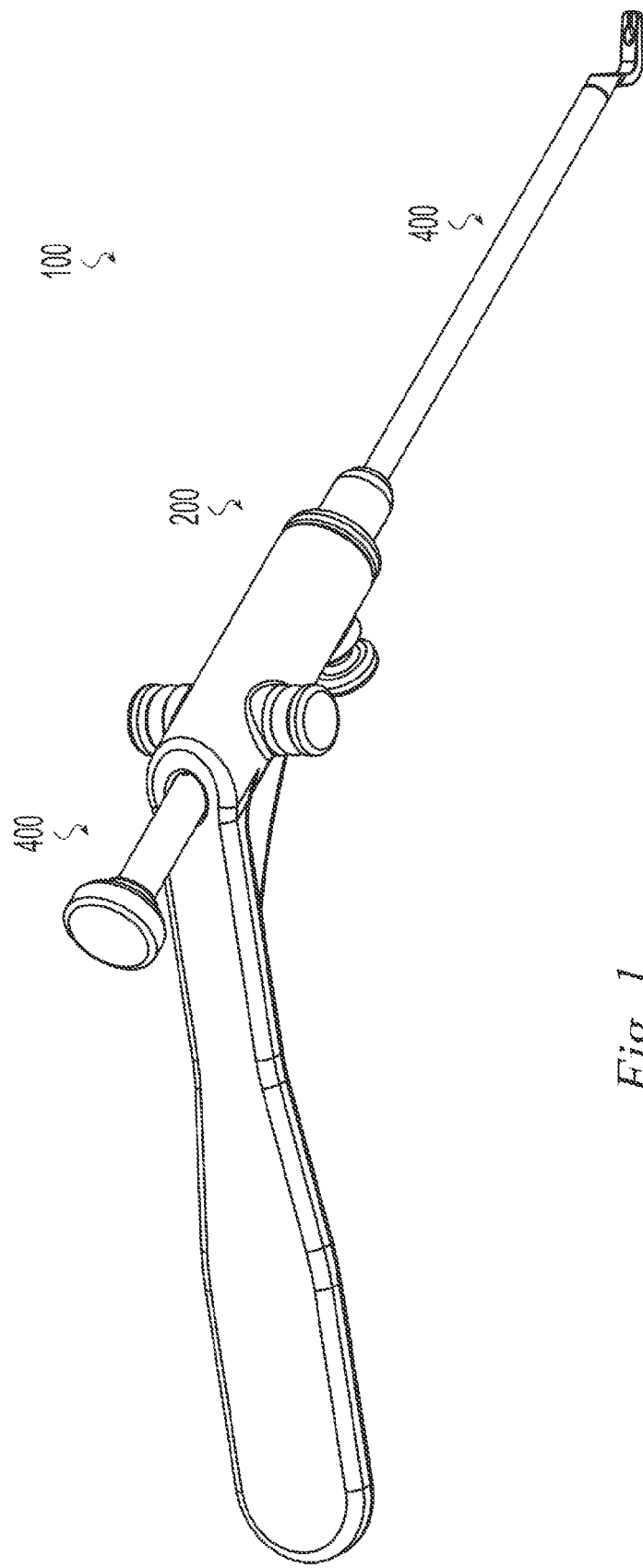
FIG. 1 is a perspective view of an illustrative example of a suture passer according to the present invention.
Figure 2:
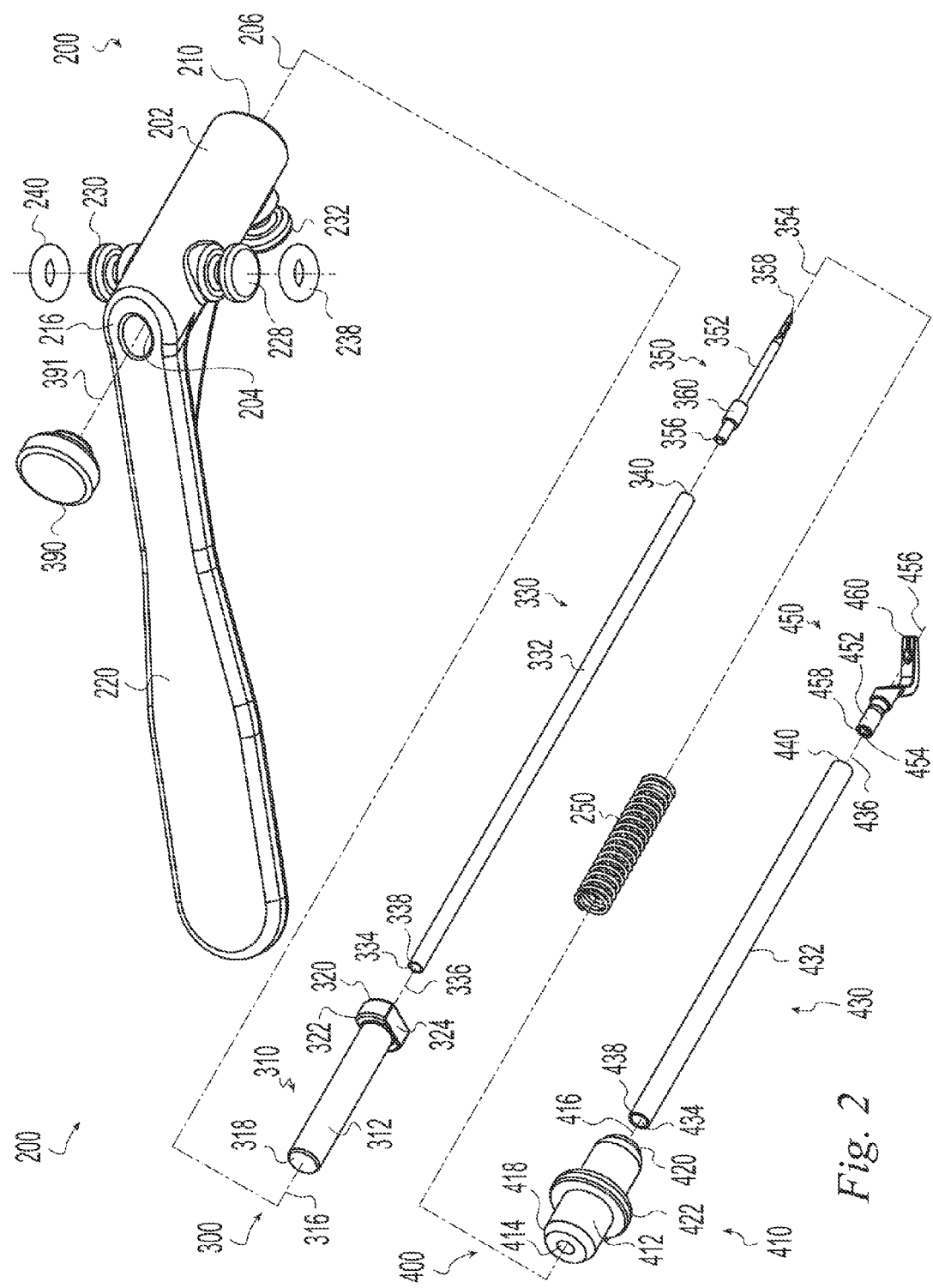
FIG. 2 is an exploded perspective view of the suture passer of FIG. 1.
Figure 4:
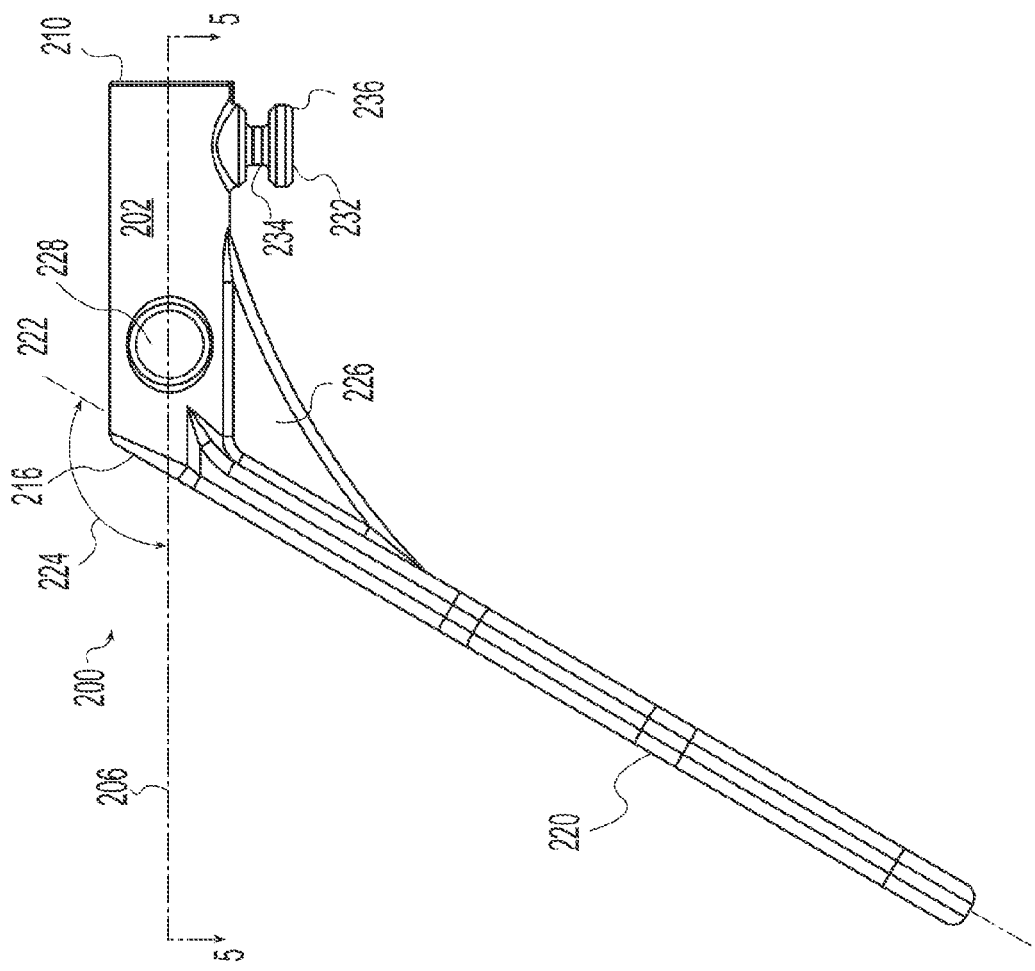
FIG. 4 is a side elevation view of the component of FIG. 3.
Figure 3:
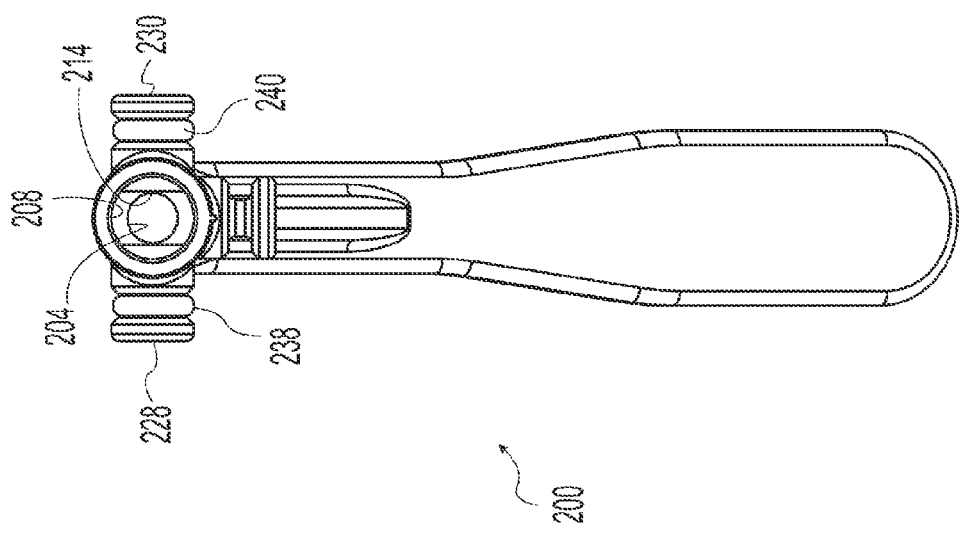
FIG. 3 is a front elevation view of a component of the suture passer of FIG. 1.
Figure 5:
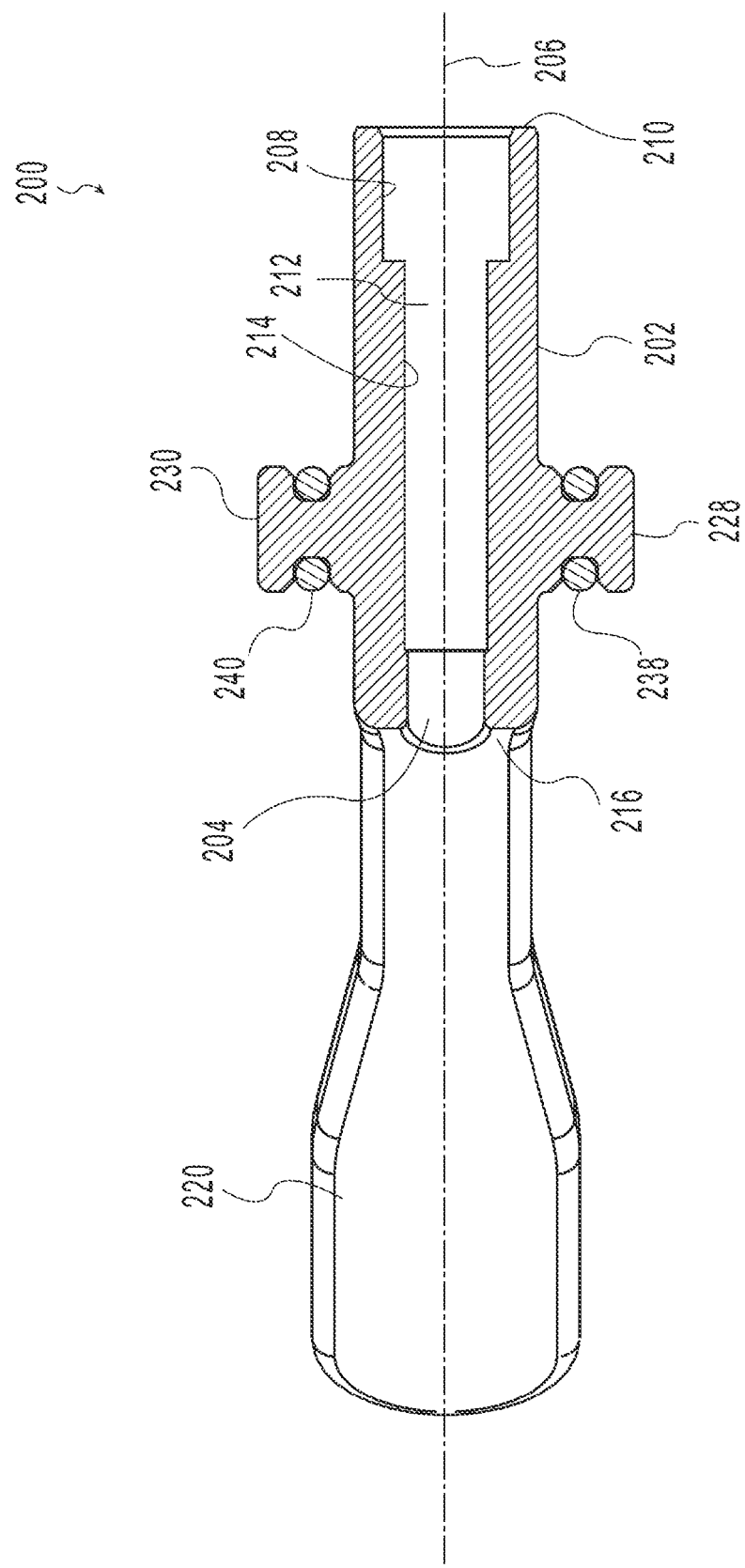
FIG. 5 is a sectional view taken along line 5-5 of FIG. 4.

The following illustrative examples depict instruments and techniques to pass a suture through a material. Instruments and techniques according to the present invention may be used to pass a suture through any material, at surgical sites anywhere in a patient's body, and for any purpose. Instruments and techniques according to the present invention are particularly useful where access to confined spaces and the ability to pass a suture through difficult to penetrate materials are needed. For example, surgery on the hands and feet often involve working in confined spaces around small joints and tough connective tissues through which it may be desirable to pass a suture. The terms "suture" and "suture strand" are used herein to mean any strand or flexible member, natural or synthetic, able to be passed through material and useful in a surgical procedure. The term "material" is used herein to mean implants, grafts, fabric, tendon, ligament, fascia, skin, muscle, bone, and any other material through which it is desirable to pass a suture. The term "transverse" is used herein to mean crossing as in non-parallel. The term "bight" is used herein to mean a bend or loop formed in the intermediate portion of a suture.

FIGS. 1-13 depict an illustrative example of a suture passer 100. The suture passer 100 includes a housing 200, a needle assembly 300, and a barrel assembly 400 mounted together and operable to translate the needle assembly 400 between a first, retracted position and a second, extended position to manipulate a suture strand.

The housing 200 includes a hollow receiver portion 202 having a hollow through bore 204 with a longitudinal bore axis 206. An enlarged counter bore 208 is formed coaxial with the through bore 204 at a distal end 210 of the receiver 202. An intermediate portion 212 of the through bore 204 has flat side walls 214. A handle 220 extends downwardly and proximally from the receiver 202 and has a longitudinal handle axis 222. The handle axis 222 forms an angle 224 with the bore axis 206. The angle 224 is in the range of 90 to 180 degrees; preferably 100 to 140 degrees; more preferably 110 to 130 degrees. In the illustrative example of FIGS. 1-3, the angle 224 is 120 degrees. A gusset 226 extends between the handle 220 and the receiver 202 for strength. One or more knobs extend from the housing to provide suture strand anchor or routing points. In the illustrative example of FIGS. 1-3, first and second opposed side knobs 228, 230 and a downwardly projecting bottom knob 232 are mounted to the receiver 202. Each knob has a narrow waist 234 and an enlarged head 236 as shown with reference to the bottom knob 232. A suture strand may be wrapped or tied around the waist 234 to secure or route the suture.

O-rings 238, 240 are provided on the side knobs 228, 230 to grip a wrapped suture to facilitate securing and removing a suture strand. As a suture is wrapped around the side knobs 228, 230, it wedges between the resilient O-ring 238, 240 and knob compressing the suture strand. The pressure of the O-ring pressing the suture strand against the knob as well as the deformation of the O-ring around the suture strand temporarily secures the suture.

The needle assembly 300 includes a piston 310, a stem 330, a needle 350, and a button 390. The piston 310 has a generally cylindrical body 312 with a longitudinal axis 316 extending from a proximal end 318 to a distal end 320. A flange 322 extends radially outwardly from the body 312 near the distal end 320. The flange has opposed flattened sides 324. A bore 326 (FIG. 8A) is formed coaxially in the piston 310 at the distal end of the body 312. The stem 330 includes an elongated hollow cylinder 332 having an outer diameter and an inner bore 334 defining a longitudinal axis 336 extending from a proximal end 338 to a distal end 340. The needle 350 is a generally cylindrical member having a shank 352 with an outer diameter defining a longitudinal axis 354 extending from a proximal end 356 to a distal tip 358. A flange 360 extends radially outwardly from the shank 352 at a position intermediate the proximal and distal ends. The needle 350 will be described in greater detail below. The button 390 has a generally cylindrical body with a longitudinal axis 391 extending from a proximal end 393 to a distal end 395. A bore 398 (FIG. 8A) is formed coaxially in the button 390 at the distal end 395 of the body. The proximal portion of the needle shank 352 fits within the inner bore 334 of the stem at its distal end 340. The stem outer diameter, near its proximal end 338, fits within the bore 326 of the piston 310. The outer diameter of the piston 310 fits within the bore 204 of the receiver 202 in linear sliding relationship. The flat sides 324 of the piston engage the flat side walls 214 of the bore 204 to prevent the needle assembly from rotating relative to the receiver 202. The piston flange 322 abuts the proximal end of the intermediate portion 212 of the bore 204 of the receiver 202 to provide a stop to needle assembly proximal translation relative to the receiver 202. The outer diameter of the piston 310, near its proximal end, fits within the bore 398 of the button 390 and the button 390 abuts a proximal end 216 of the receiver to provide a stop to needle assembly distal translation relative to the receiver 202. The joints between the button 390 and piston 310, the piston 310 and the stem 330, and stem 330 and needle 350 are secured by pressing, gluing, pinning, welding, or other suitable securing means. Alternatively, two or more of these components or various combinations of them may be made as a single piece.

The barrel assembly 400 includes a barrel bushing 410, a barrel 430, and a foot 450. The bushing 410 has a generally cylindrical body 412 having a through bore 414 with a longitudinal axis 416 extending from a proximal end 418 to a distal end 420. A flange 422 extends radially outwardly from the body 412 at a position intermediate the proximal and distal ends. An enlarged counter bore 424 (FIG. 8A) is formed coaxial with the through bore 414 at the distal end 420 of the body 412. The barrel 430 includes an elongated hollow cylinder 432 having an outer diameter and an inner bore 434 defining a longitudinal axis 436 extending from a proximal end 438 to a distal end 440. The foot 450 is a generally hook-shaped member having a hollow post 452 having an outer diameter and an inner bore 454 defining a longitudinal axis 456 extending from a proximal end 458 of the cylinder to a distal end 460 of the foot 450. The foot will be described in greater detail below. The foot post 452 outer diameter fits within the inner bore 434 of the barrel at its distal end 440. The barrel 430 outer diameter, near its proximal end 438, fits within the counter bore 424 of the bushing. A coiled compression spring 250 fits coaxially over the needle assembly 300 within the bore 204 of the receiver 202 and rests against the distal end of the piston flange 322. The barrel assembly 400 fits coaxially over the needle assembly 300 and the outer diameter of the bushing 410, near its proximal end 418, fits within the counter bore 208 of the receiver 202 and is pressed proximally until the flange 422 abuts the receiver distal end 210. The proximal end of the bushing retains the spring 250 within the bore 204. The joints between the foot 450 and barrel 430, the barrel 430 and bushing 410, and the bushing 410 and receiver 202 are secured by pressing, gluing, pinning, welding, or other suitable securing means. Alternatively, the bushing, barrel, foot, or any combination of them may be made as a single piece.

Pressing the button 390 distally translates the needle assembly from a first, proximal, retracted position distally along the needle axis 354 compressing the spring 250 and extending the needle 350 through the foot 450 to a second, distal, extended position. Releasing the button 390 allows the spring 250 to expand and bias the needle assembly 300 back toward the first position. The needle assembly 300 of the illustrative example of FIGS. 1-13 is a linear arrangement mounted for linear, coaxial translation in the housing 200 and barrel assembly 400 with the needle projecting straight through the foot to increase rigidity and power facilitating driving the needle 350 through difficult to penetrate materials and access confined spaces. The barrel 430 may have a circular, polygonal, or any other cross sectional shape.

Figures 8A, 8B, 8C:
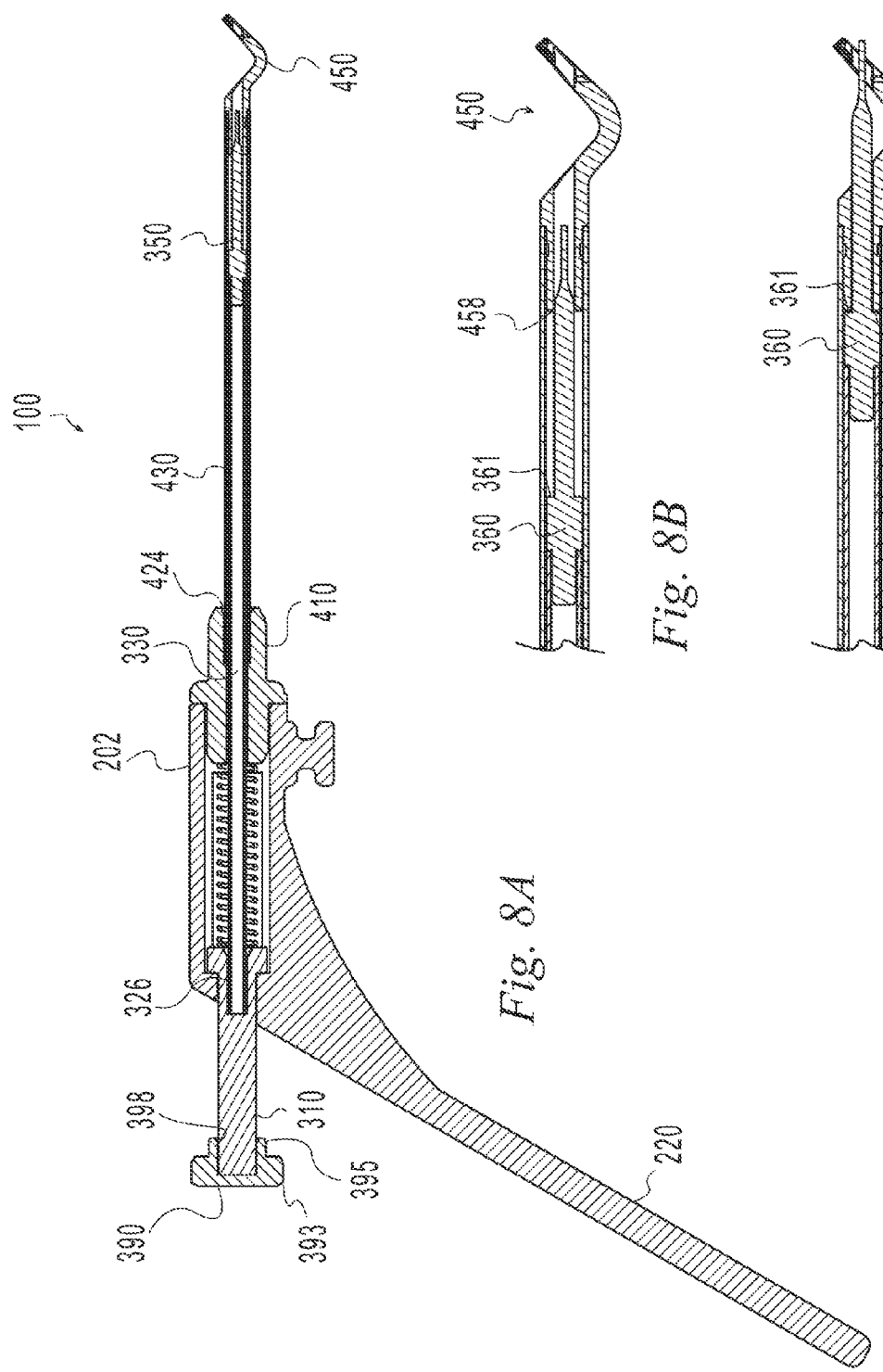
FIG. 8A is a sectional view taken along line 8-8 of FIG. 7.
FIGS. 8B and 8C are sectional detail views of the distal end of the suture passer of FIG. 1 illustrating an operating feature.

A distal facing shoulder 361 on the needle shank 352 may be arranged to abut the proximal end 458 of foot 450 to provide an alternative stop to the distal translation of the needle as shown in FIGS. 8B and 8C. With the needle distal translation controlled by abutment of the needle and foot, the tolerance stack up of the rest of the suture passer assembly is eliminated from the needle depth control. In this way the needle distal translation may be more tightly controlled despite manufacturing tolerances in the various suture passer components.

FIGS. 9 and 10 illustrate the foot 450 of the illustrative example of FIGS. 1-13 in greater detail. The hooked portion of the foot 450 includes an elbow 462 having a first, proximal portion 464 extending distally from the post 452 along a proximal portion axis 465 diverging from the bore axis 456 at a first angle 466 relative to the bore axis 456. A second, distal portion 468 extends distally from the first portion 464 along a distal portion axis 469 converging toward the bore axis 456 at a second angle 470 relative to the bore axis 456. The first and second angles 466, 470 are chosen to allow the foot to extend into a confined space, for example behind material such as a portion of soft tissue such as a tendon or ligament, and position the receiver 202 so as not to obstruct the users view of the foot and needle. The first angle 466 is in the range of 0 to 180 degrees; preferably 0 to 90 degrees; preferably less than 90 degrees; more preferably 25 to 65 degrees; more preferably 35 to 45 degrees. In the illustrative example of FIGS. 9 and 10, the first angle 466 is approximately 42 degrees. The second angle 470 is in the range of 0 to 90 degrees; preferably 25 to 65 degrees; more preferably 35 to 45 degrees. In the illustrative example of FIGS. 9 and 10, the second angle 470 is also approximately 42 degrees.

The distal portion 468 of the foot 450 includes a proximal facing surface 474 having first and second opposing lateral borders 487 and 488 and a distal border 489 at the distal end 460. The distal portion 468 has a length 490 from the distal border 489 to the elbow 462 and a width 491 between the lateral sides on the proximal facing surface. The distal portion axis 469 extends in the length direction and in the illustrative example of FIGS. 9 and 10 the length is greater than the width. In the illustrative example of FIGS. 9 and 10, the lateral borders 487 and 488 are parallel to one another. However, it is contemplated that the borders may converge or diverge. The lateral borders 487 and 488 define a foot profile projected parallel to the foot bore axis 456.

An opening or eye 472 is formed through the distal portion 468, from the proximal facing surface 474 to a distal facing surface 476, between the lateral borders 487, 488 and coaxial with the bore axis 456 for receiving the distal end of the needle 350 when the needle is in the second position. The proximal facing surface 474 defines a proximal facing surface plane that the needle crosses when it is received by the eye 472. A hole 478 defining a hole axis 480 extends through the second portion 468 from the distal surface 476 and intersecting the eye 472. The hole 478 permits passing a suture strand from the distal surface 476 of the second portion 468 to the eye 472. The hole axis 480 forms an angle 482 relative to the bore axis 456. The angle 482 is between parallel to the proximal facing surface 474 of the second portion 468 and parallel to the distal facing surface of the first portion 464; preferably in the range of 45 to 135 degrees; more preferably 45 to 90 degrees. In the illustrative example of FIGS. 9 and 10, the hole angle 482 is approximately 90 degrees relative to the bore axis 456. A groove 484 is formed in the proximal surface 474 of the second portion 468 communicating from the eye 472 to the distal end 460. A notch 486 is formed in the distal border 489 through the distal end 460 from the proximal surface 474 to the distal surface 476 and communicating with the groove 484. The hole 478, groove 484 and notch 486 define a suture path in the foot 450 and are sized to receive a suture strand and retain the strand on the distal end of the foot 450. In the illustrative example of FIGS. 9 and 10, the suture path lies in a suture path plane that is coplanar with the foot bore axis 456 (which is coaxial with the motion axis 506 as described below relative to the operation of the suture passer) and the distal portion axis 469. As seen in FIG. 10A, the foot 450 projects a material (e.g. tissue) receiving hook shape in a foot side plane parallel to the suture path plane; i.e. perpendicular to the foot bore axis 456 and the distal portion axis 469. The interior of the hook is bounded by the distal facing surface 492 of the first or proximal portion 464 of the foot, the elbow 462, and the proximal facing surface 474 of the second or distal portion 468 of the foot. The proximal surface 474 of the second portion 468 of the foot 450 provides a supporting platform for material through which the needle 350 is passed. The eye 472 allows the needle 350 to penetrate all the way through the material and intercept a suture strand extending from the hole 478 to the groove 484.

Figure 11:
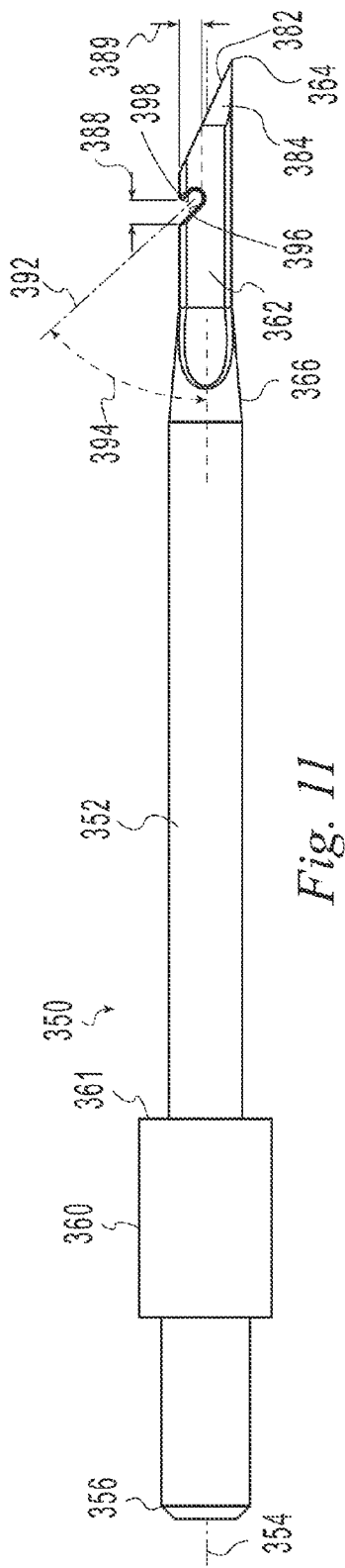
FIG. 11 is a bottom plan view of a component of the suture passer of FIG. 1.
Figure 12:
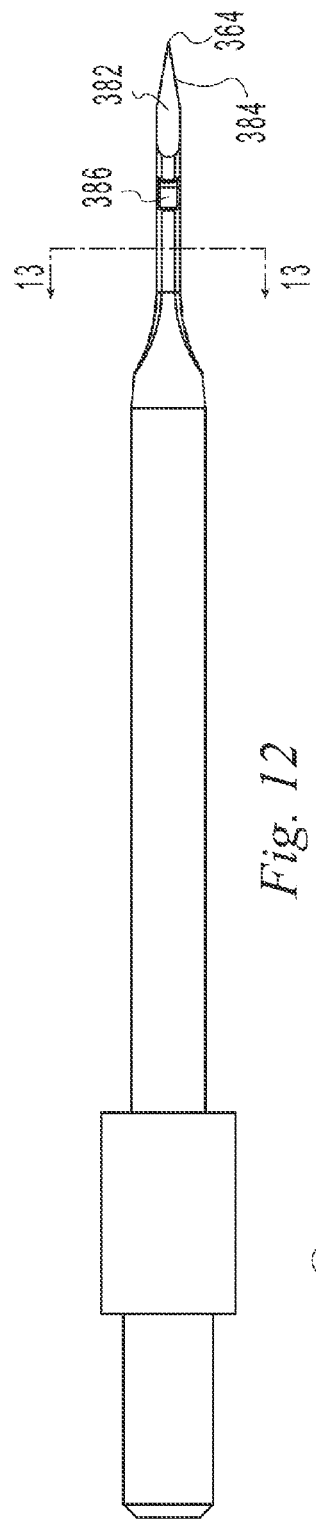
FIG. 12 is a side elevation view of the component of FIG. 11.
Figure 13:
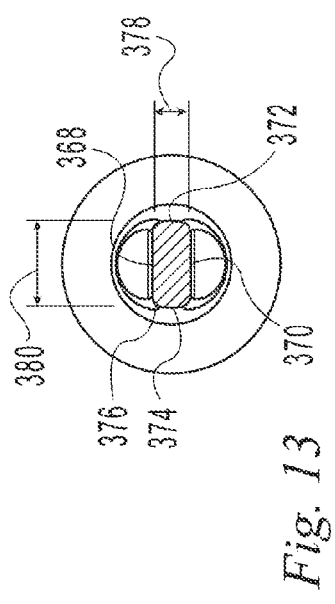
FIG. 13 is a sectional view taken along line 13-13 of FIG. 12.
Figure 14A:
FIGS. 14A-G are bottom plan views of variations of the component of FIG. 11.
Figure 14B:
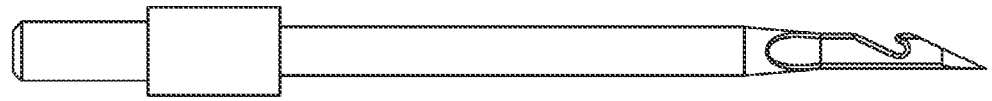
Figure 14C:
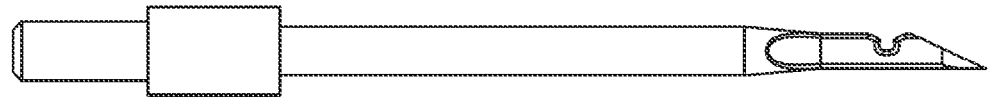
Figure 14D:
Figure 14E:
Figure 14F:
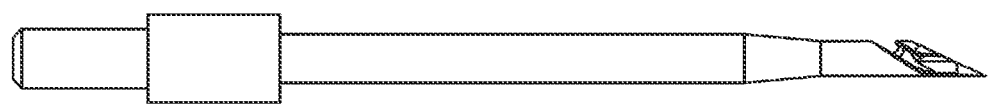
Figure 14G:
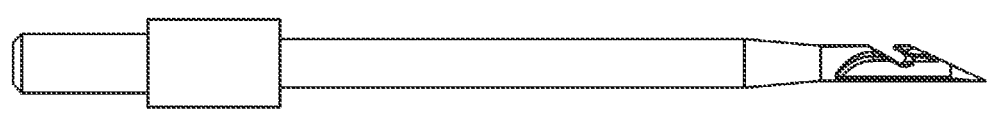

FIGS. 11-13 illustrate the needle 350 of the illustrative example of FIGS. 1-13 in greater detail. A narrowed shaft 362 extends between the shank 352 and a sharp tip 364 at the distal end of the needle. A shoulder 366 defines the transition from the shank 352 to the shaft 362. The shaft 362 is generally rectangular in cross section with a top 368, a bottom 370, and opposing sides 372, 374. The corners 376 are rounded. The shaft 362 has a height 378 between the top 368 and bottom 370 and a width 380 between the sides 372, 374. Both the height 378 and width 380 of the shaft are narrower than the shank 352. The width 380 of the shaft 362 is greater than its height 378. The ratio of the width 380 to the height 378 is in the range of 1 to 3; preferably 2 to 3. In the illustrative example of FIGS. 11-13 the ratio is approximately 2.3. The distal end of the shaft is tapered in the width dimension from the full width to the tip 364. In the illustrative example of FIGS. 11-13, the shaft is tapered on a single side in the width dimension to form a single-sided bevel 382. The distal end of the shaft is tapered in the height dimension from the full height to the tip 364. In the illustrative example of FIGS. 11-13, the shaft is tapered on opposite sides in the height dimension to form a chisel portion 384. A notch 386 is formed in the side of the shaft 362 through the shaft 362 from the top 368 to the bottom 370. The notch 386 has an opening width 388 measured parallel to the needle axis 354, a depth 389 measured perpendicular to the needle axis 354, and a notch axis 392 forming an angle 394 to the needle axis 354. In the illustrative example of FIGS. 11-13, the notch has parallel side walls 396, 398 that are parallel to the axis 392. The notch width 388, depth 389, and angle 394 are selected to optimize the ability of the needle 350 to capture and retain a suture strand while avoiding snagging other material through which the needle 350 passes. FIGS. 14A-14G illustrate a variety of needle designs having varying notch width, depth, and angle. The present inventors have determined that the balance between capturing and retaining a suture strand and avoiding snagging is optimized, in the case of a suture strand with a diameter D, when the width of the notch is in the range of 0.9D to 2D. A notch width of 0.9D creates a press fit depending on the resilient nature of the suture strand. Preferably, the notch width is in the range of 1D to 1.5D. Similarly, the notch depth is optimized when the depth is in the range of 0.75D to 3D. A notch depth of 0.75D captures the suture but leaves a portion of the suture projecting from the notch. Preferably, the depth is in the range of 1D to 2D. The notch angle is in the range of 30 to 90 degrees; preferably 35 to 55 degrees. In the illustrative example of FIGS. 11-13, the notch was optimized for a USP#2-0 suture having a diameter in the range of 0.300-0.339 mm and has a width of 0.30 mm and a depth of 0.46 mm and an angle of 45 degrees. The notch opens toward the side of the needle 350 and suture passer 100. The bevel 382 leads from the tip 364 of the needle along the narrow side of the needle shaft 362 toward the opening of the notch 386. The needle may be sized to capture and pass one or more suture strands.

FIGS. 15-21 illustrate loading a suture strand 500, having a first end 502 and a second end 504 into the suture passer 100 of FIGS. 1-13. A first end 502 of the suture strand 500 is inserted through the hole 478 in the foot 450 from the distal surface 476 toward the eye 472 and extended past the proximal surface 474 as shown in FIGS. 15 and 16. The first end 502 of the suture strand is pulled distally to place the suture strand 500 in the groove 484 as shown in FIGS. 17 and 18. The suture strand 500 is wrapped over the distal end 460 in the notch 486 and pulled proximally over the distal surface 476 of the second portion of the foot 450 as shown in FIGS. 19 and 20. In the illustrative example of FIGS. 15-21, the suture path defined by the hole 478, groove 484, and notch 486 includes a first turning point 493 (FIG. 19) and a second turning point 494. The first and second turning points are contained within the foot profile bounded by the first and second lateral borders 487 and 488. The suture is wrapped over a portion of the foot and the wrapped portion is likewise contained within the foot profile bounded by the first and second lateral borders 487 and 488 as seen in FIGS. 20A and 20B. Since the suture path does not cross the lateral borders, or side surfaces of the foot, the foot profile remains narrow in the width dimension with a suture loaded. Furthermore, in the illustrative example of FIGS. 15-21, no portion of the suture extends into the interior of the hook shaped foot defined by the distal facing surface 492, elbow 462, and proximal facing surface 474 as seen in FIG. 19. Therefore there is no suture in the hook to interfere with getting material fully within the hook and there is no impingement of material on the suture that might tend to dislodge suture from the suture path. Finally, in the illustrative example of FIGS. 15-21, the hole 478 fully encloses the suture capturing the suture proximal the eye 472 and the groove 484 partially encloses the suture, being open on the top, capturing the suture distal the eye permitting one end of the suture to be released from the foot of the suture passer after a stitch is completed while positively retaining the other end.

Figure 21:
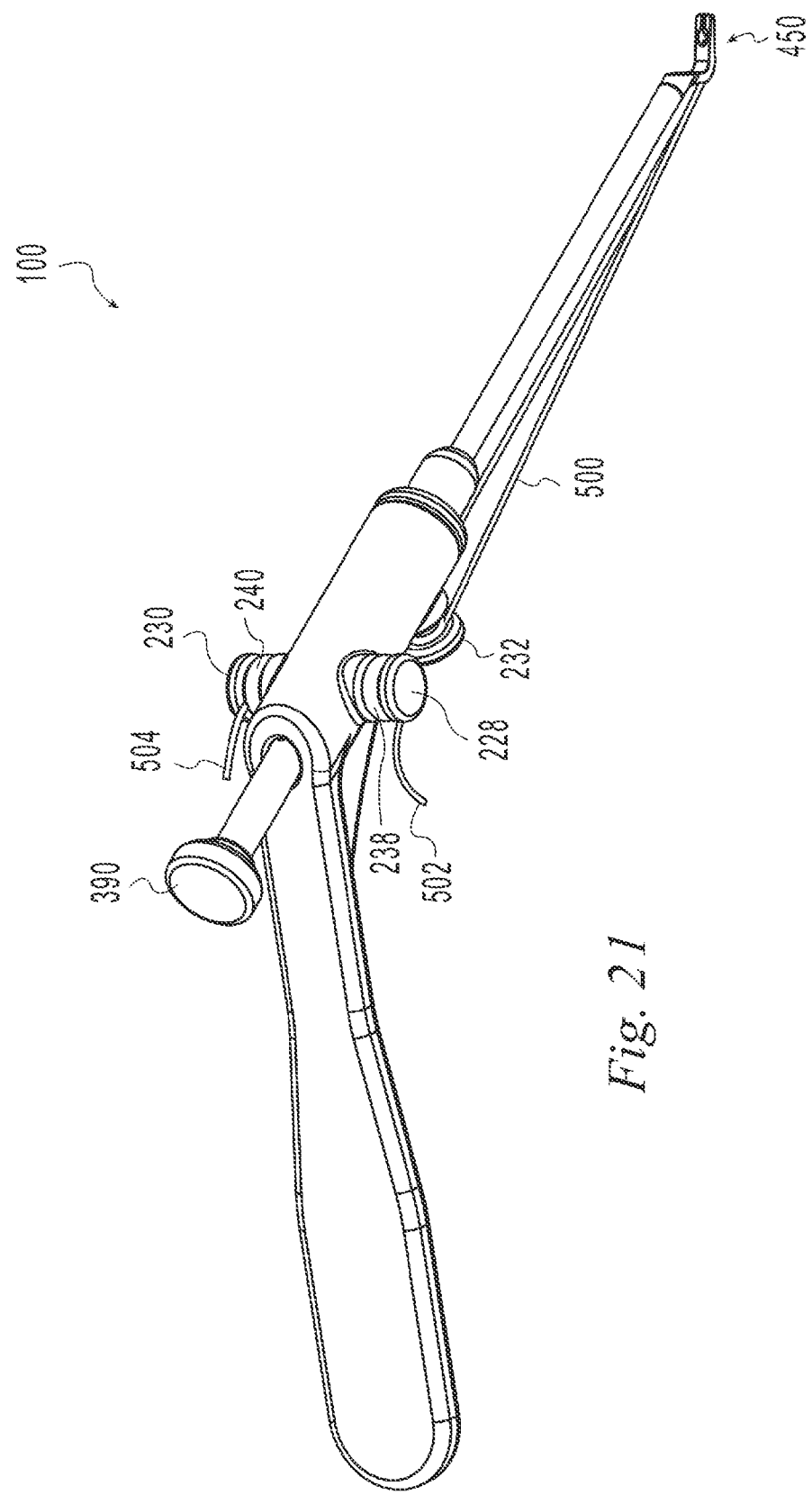
FIG. 21 is a perspective view of the suture passer of FIG. 1 illustrating a suture being loaded on the suture passer.
Figure 27:
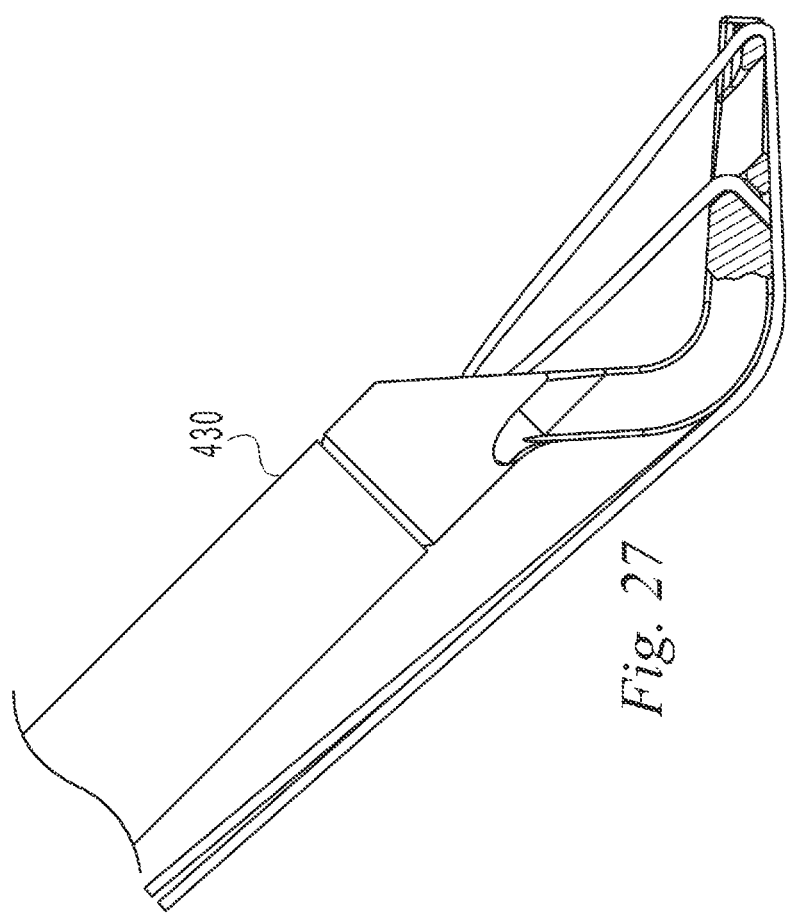
FIG. 27 is a partially sectioned side elevation view of the distal end of the suture passer of FIG. 1 illustrating the operation of the suture passer.

The ends 502, 504 of the suture strand are wrapped around the side knobs 228 and 230 and retained by the O-rings 238, 240. In the example of FIG. 21, the suture strand ends are routed proximally to the bottom knob 232 wrapped part-way around the proximal side of the knob 232 and secured on the side knob opposite the side on which the end was routed such that the suture strand is maintained near the center of the suture passer 100 and better retained on the foot 450.

FIGS. 22-27 illustrate the operation of the suture passer 100. When the button 390 is pressed distally, the needle assembly 300 moves distally relative to the housing and barrel assembly along the straight-line motion axis 506 of the suture passer which is coaxial with the needle axis 354 and foot bore axis 456. As the needle 350 approaches the suture strand 500, the bevel 382 contacts the suture strand 500 and wedges it sideways increasing the tension in the suture as shown in FIGS. 22 and 23. Further advancement of the needle 350 moves the notch 386 toward alignment with the suture strand 500 until the tension in the suture causes the suture 500 to move into the notch 386 as shown in FIGS. 24 and 25. Releasing pressure on button 390 allows the spring 250 to bias the needle assembly proximally. Depending on the resilience of the suture 500 and how tightly it is secured to the knobs 228, 230, the needle may or may not be able to retract. By releasing one or both ends 502, 504 of the suture 500, the suture ends can move toward the foot 450 and allow the needle to retract and pull a bight 508 of suture 500 proximally toward the barrel 430 as shown in FIG. 26. Further retraction of the needle 350 pulls the bight 508 into the barrel 430 (FIG. 27) trapping the bight 508 between the needle 350 and barrel bore 434. To release the bight 508, the button 390 is pressed to advance the needle 350 out of the barrel 430 and the suture may be dislodged from the needle notch 386. In the illustrative example of FIGS. 22-27, the needle is contained within the foot profile bounded by the first and second lateral borders 487 and 488 and projected parallel to the motion axis 506 as seen in FIGS. 23A and 23B. With the needle contained within this profile, the needle does not impinge or snag on material on the sides of the foot 450.

Figure 28:
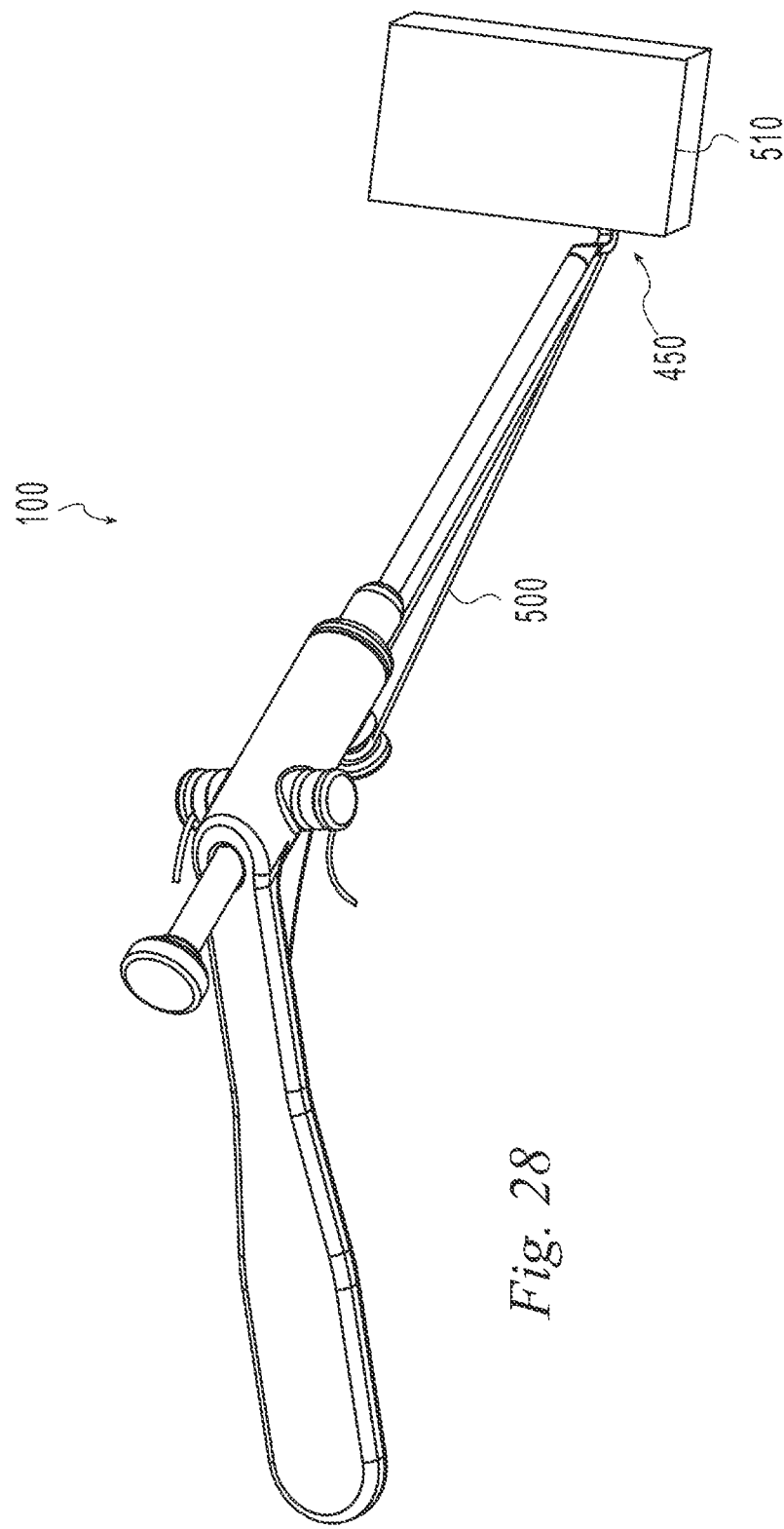
Figure 29:
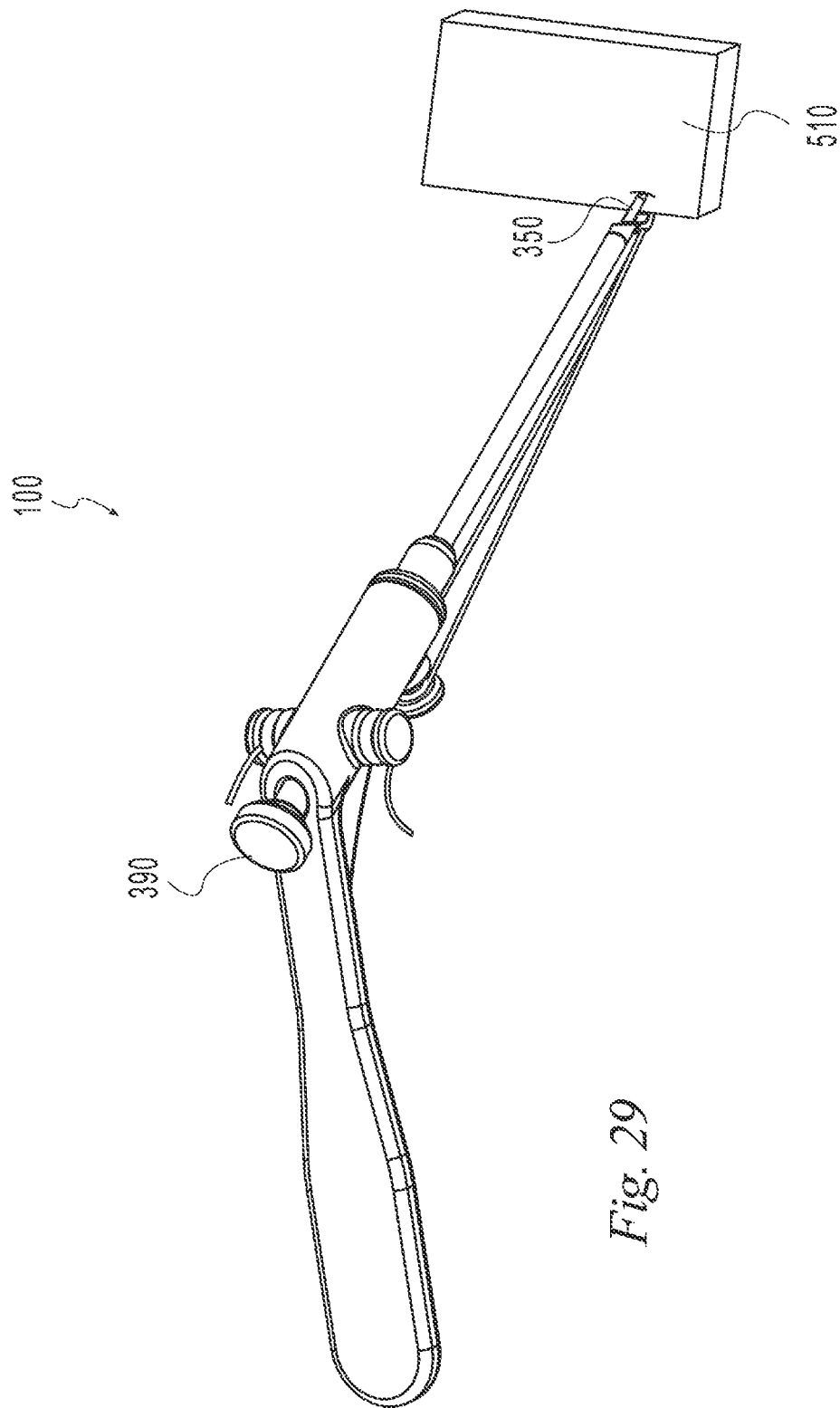

FIGS. 28-46 depict examples of the illustrative suture passer 100 in use to pass sutures through a material to create a variety of stitches. Referring to FIG. 28, the suture passer has been loaded as described relative to FIGS. 15-21. The foot 450 is positioned adjacent material 510 through which it is desired to pass the suture 500. The second portion 468 of the foot is positioned behind the material 510 with the proximal surface 474 supporting the material 510. Referring to FIG. 29, the button 390 is pressed to advance the needle 350 through the material 510 and capture the suture 500 in the eye 472 of the foot 450. Referring to FIG. 30, the button 390 has been released and the suture ends 502 and 504 have been freed from the knobs 228, 230 and allowed to move distally so that the needle 350 has retracted and pulled a bight 508 of suture 500 through the material 510. Referring to FIG. 31, the button 390 has been pressed to release the bight 508 and the first end 502 has been allowed to drop free from the passer 100. Referring to FIGS. 32 and 33, the second end 504 has been removed from the foot 450 by pulling the passer 100 proximally away from the bight or by pulling the suture 500 distally away from the foot 450. The suture ends 502, 504 have been passed through the bight 508 and pulled to form a stitch in the form of a hitch 512.

Referring to FIG. 34, instead of pulling the ends 502, 504 through the bight 508, the first end 502 has been pulled through the material 510 by pulling on one side of the bight 508 to form a simple stitch 514.

Figure 35:
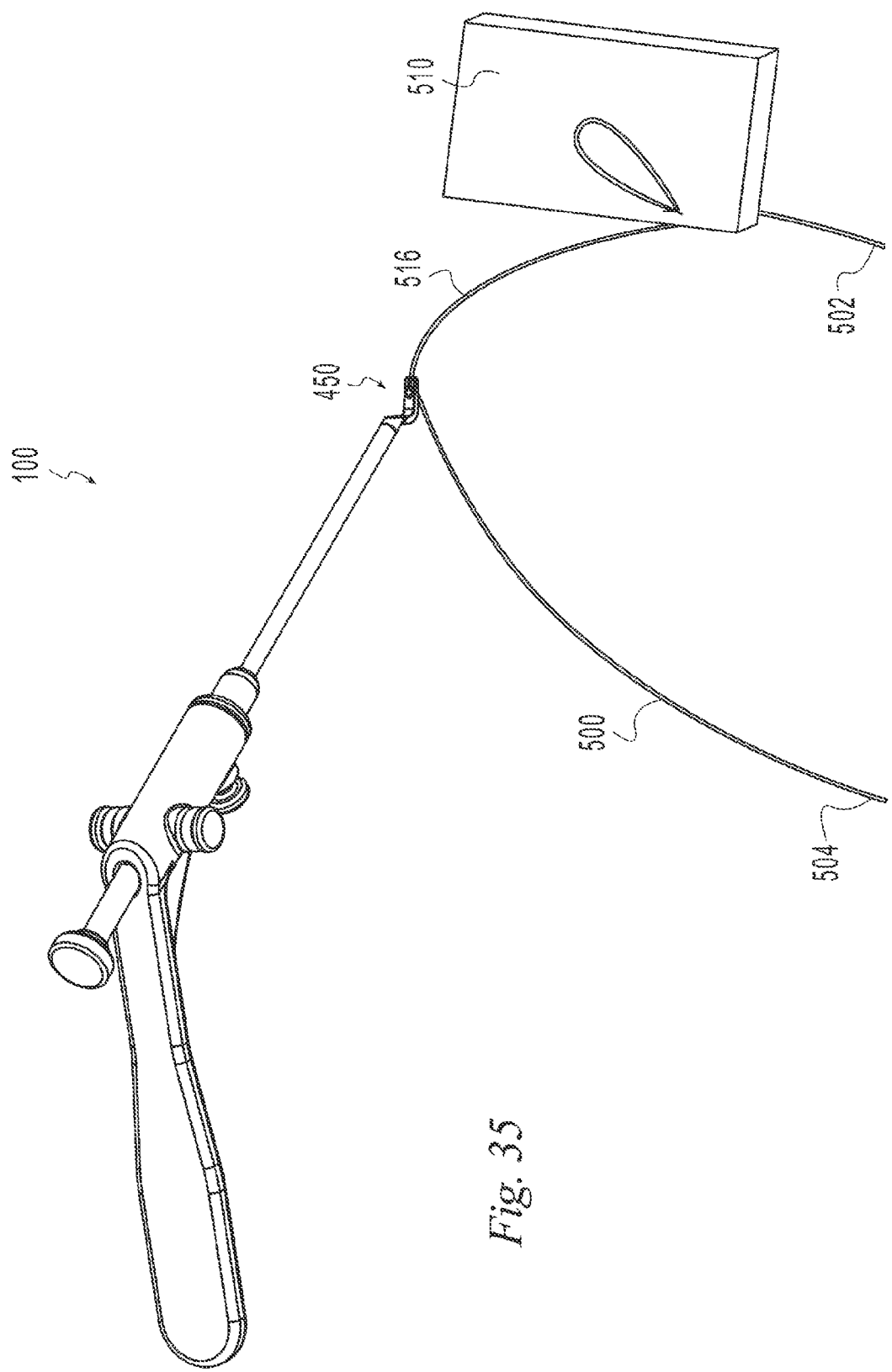
Figure 36:
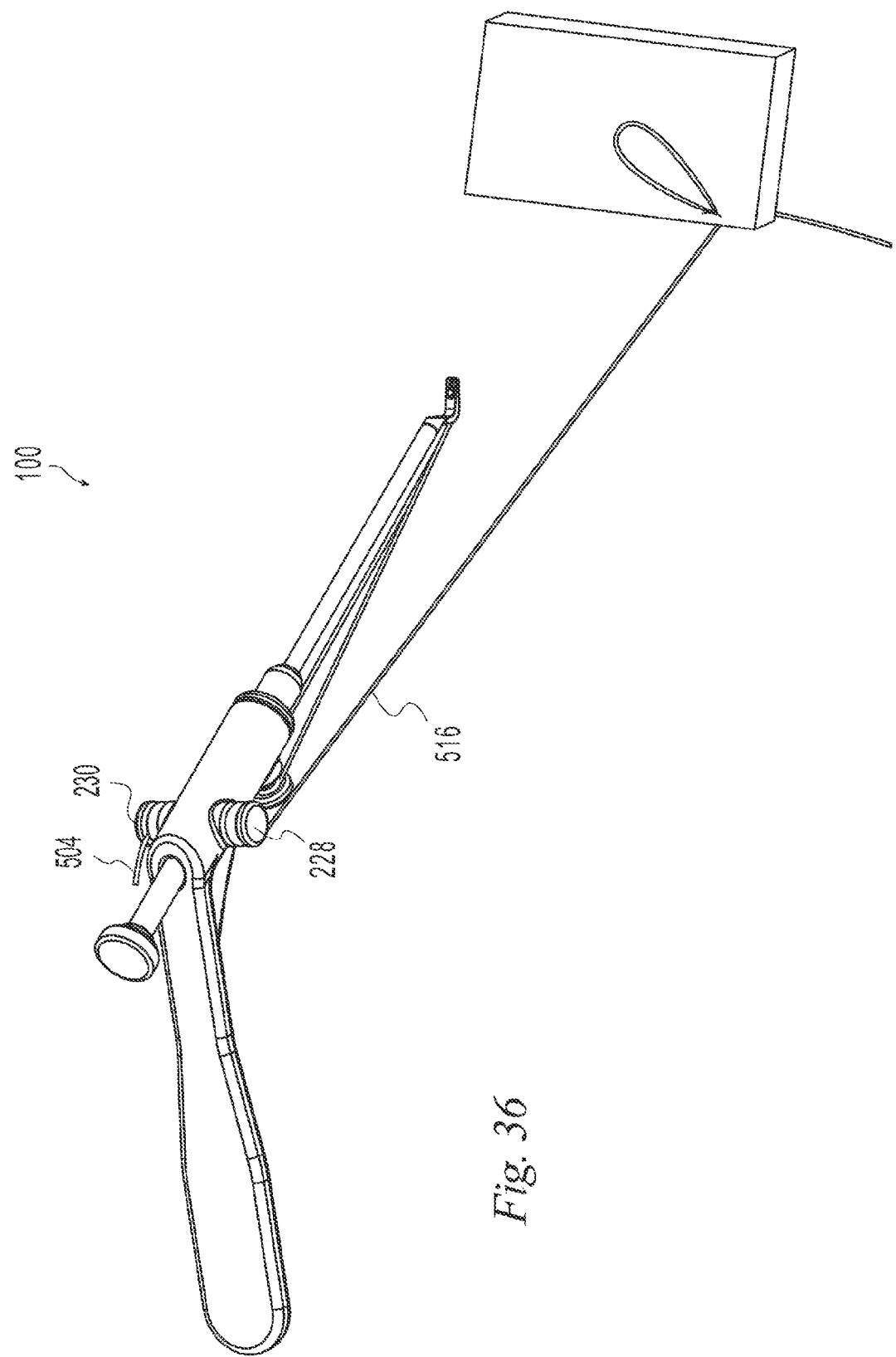
Figure 37:
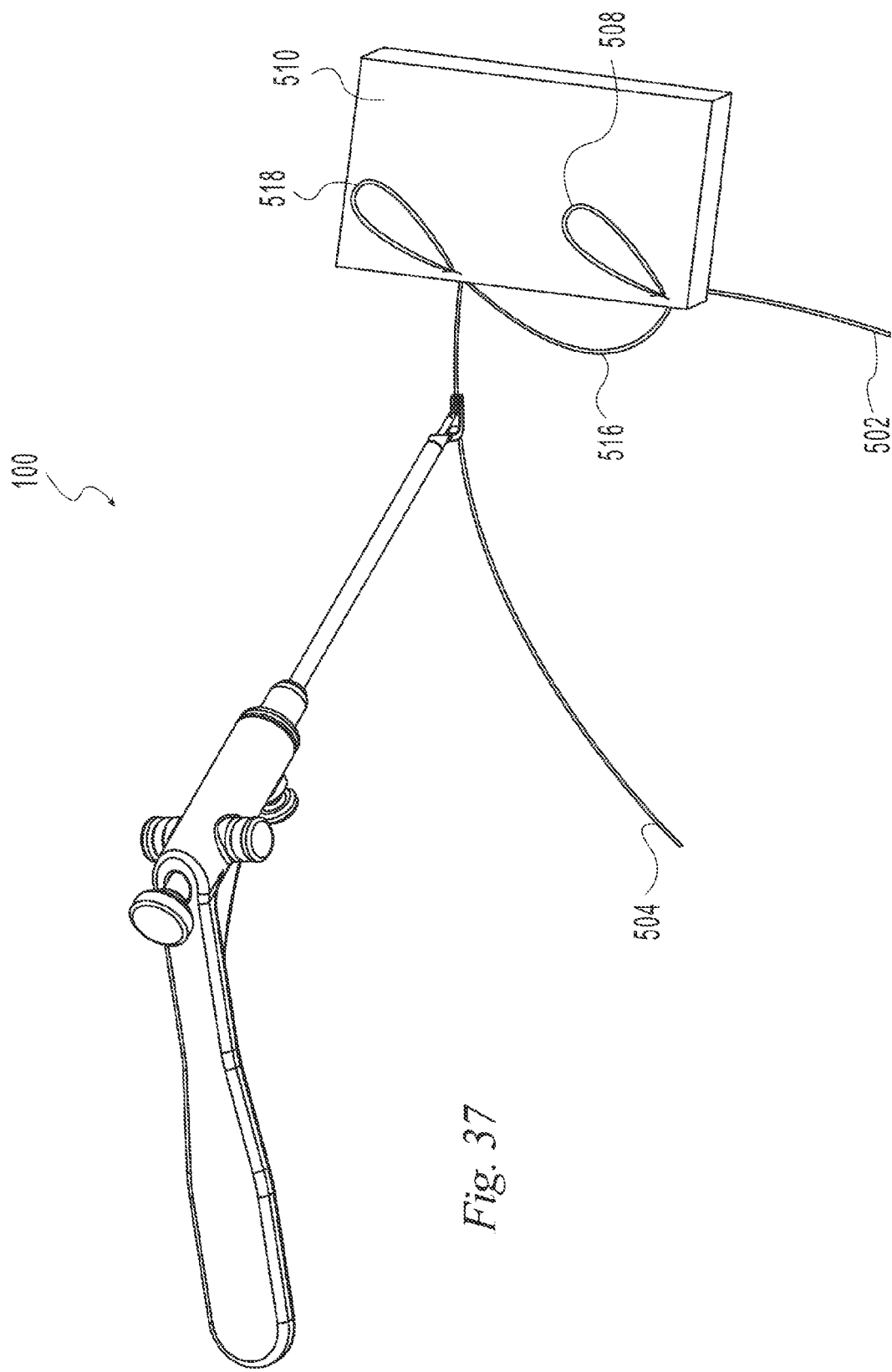

Referring to FIG. 35, the passer 100 is prepared for making a running stitch by pulling suture 500 distally through the foot to create slack 516 between the foot 450 and material 510. Referring to FIG. 36, the slack 516 and the second end 504 have been pulled proximally and secured to the knobs 228, 230. Referring to FIG. 37 a second bight 518 has been passed through the material 510 in the same manner as the first bight 508 and the slack 516 and second end 504 have been released from the passer 100.

Figure 38:
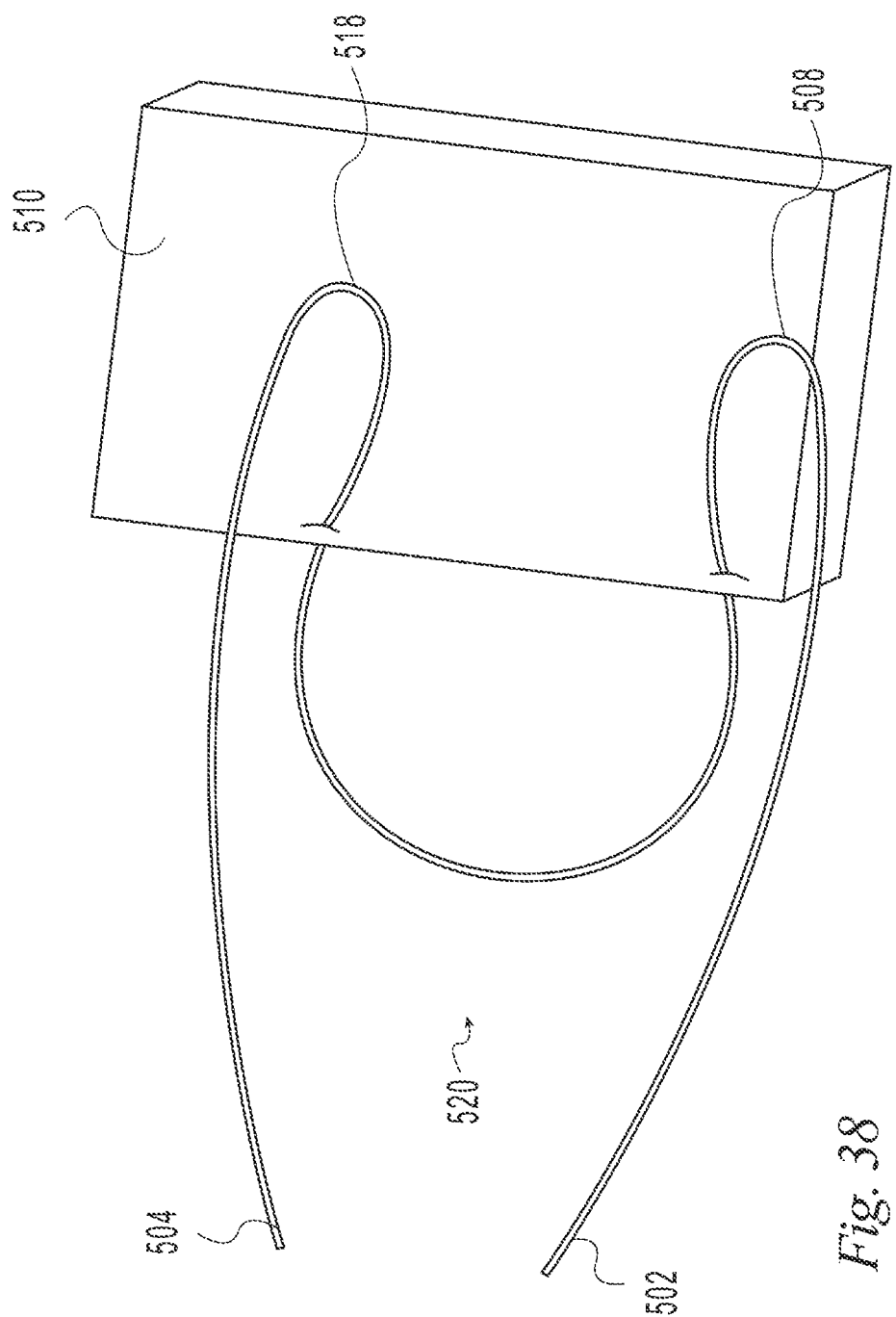

Referring to FIG. 38, the first and second ends 502, 504 have been pulled through to the front side of the material 510 by pulling on one side of each of the bights 508, 518 to form a mattress stitch 520 in the material 510.

Figure 39:
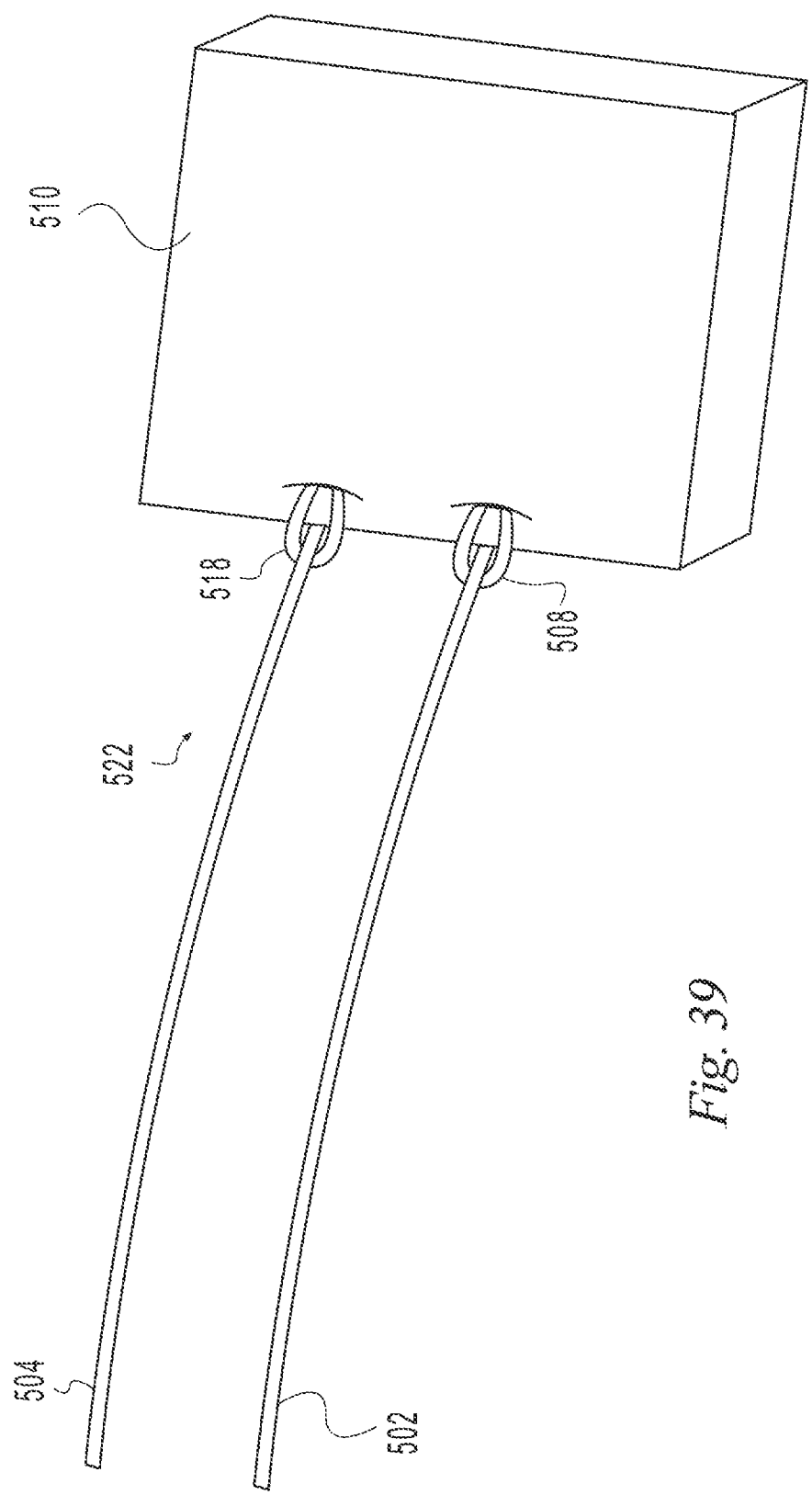

Referring to FIG. 39, instead of the ends 502, 504 being pulled through the material the first end 502 has been placed through the first bight 508 and the second end 504 has been placed through the second bight 518 to form a modified mattress stitch 522 with each end 502, 504 secured by a hitch.

Figure 40:
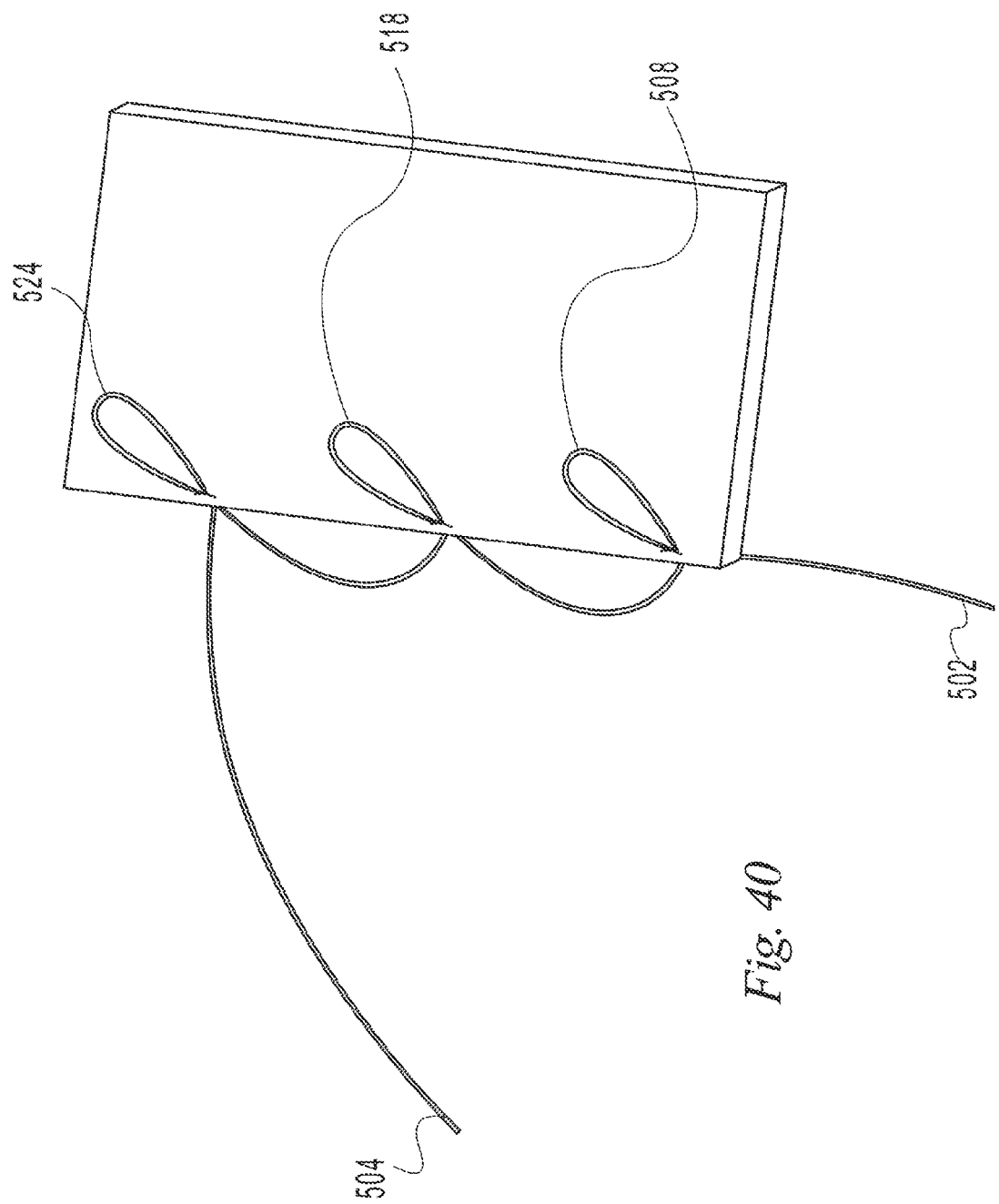
Figure 41:
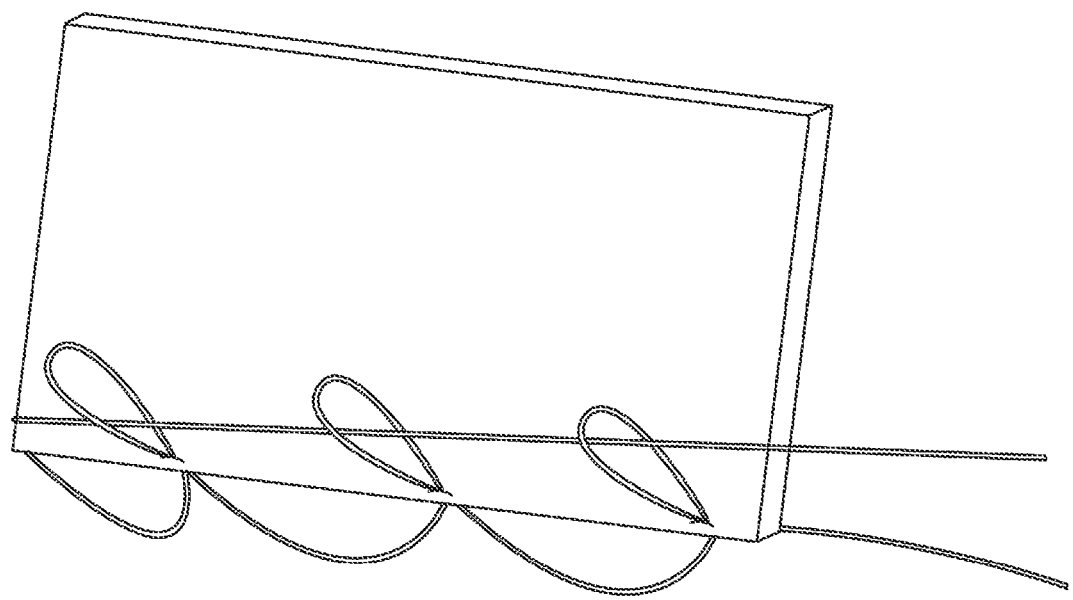

Referring to FIG. 40, a third bight 524 has been pulled through the material in the same manner as the first two bights 508, 518. A stitch may be formed by placing one or both ends 502, 504 through the bights 508, 518, 524 to lock the bights as shown in FIG. 41.

Figure 42:
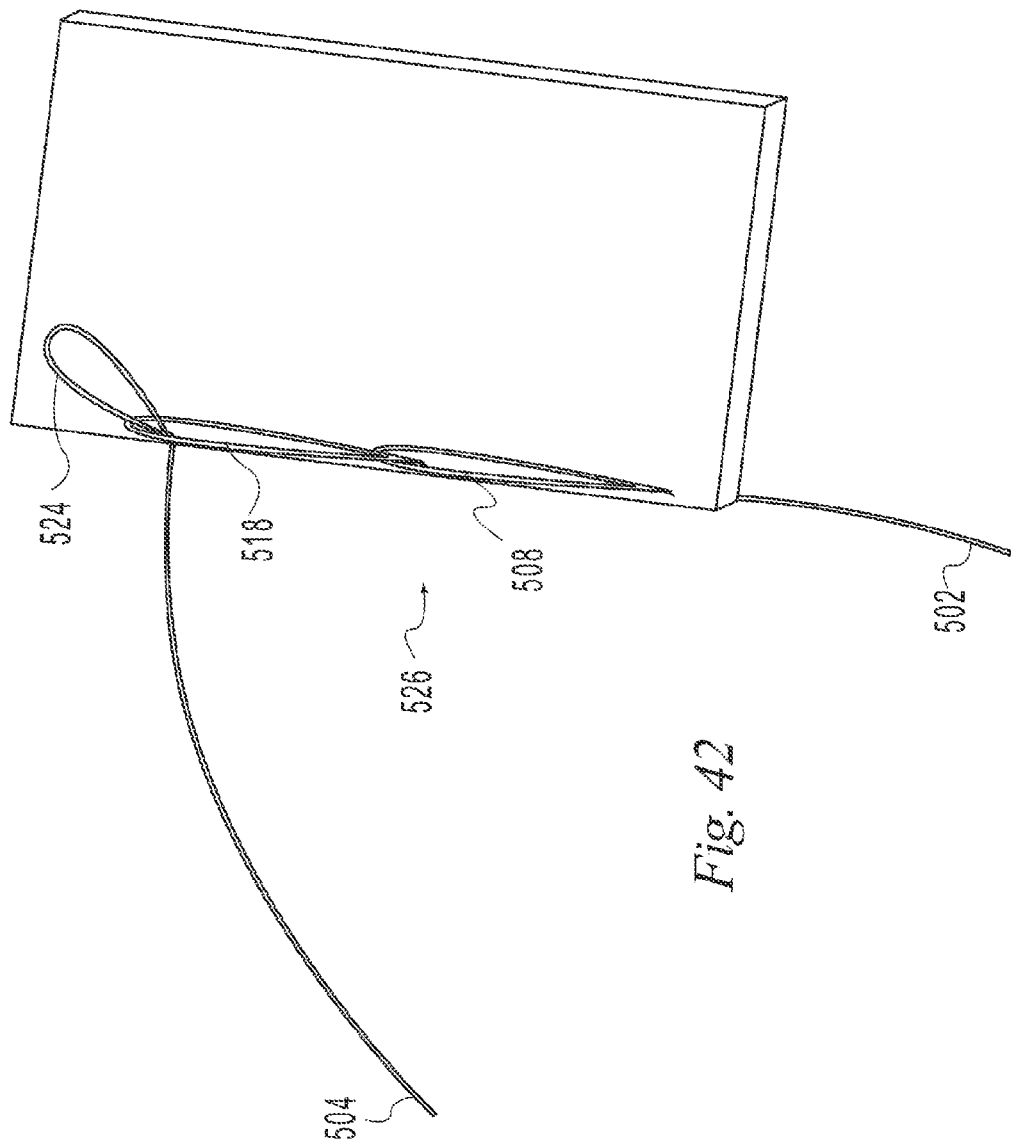

Referring to FIG. 42, instead of placing the ends through the bights, the second bight 518 has been looped through the first bight 508, and the third bight 524 has been looped through the second bight 518 to form a chain stitch 526.

Figure 43:
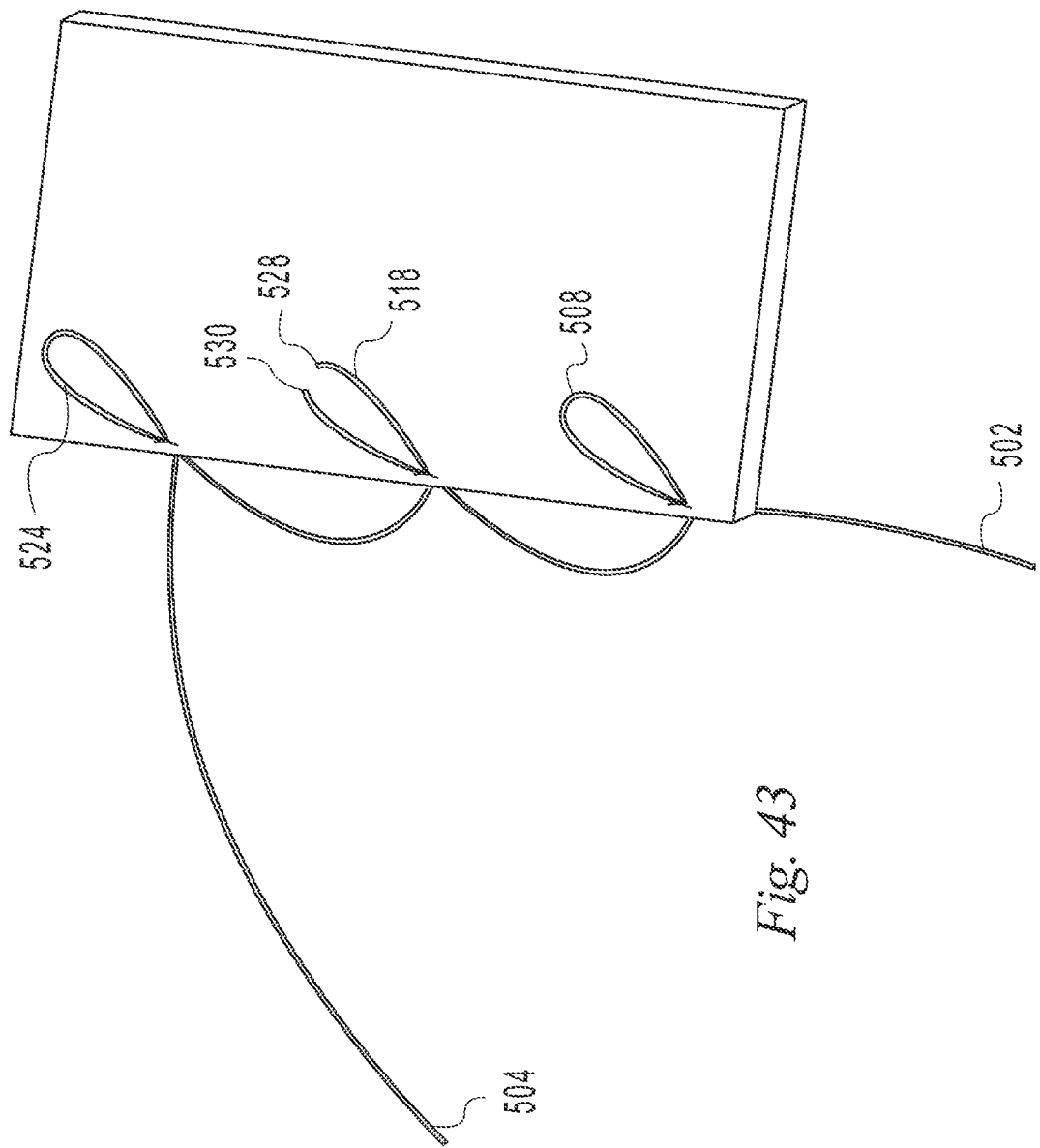
Figure 47:
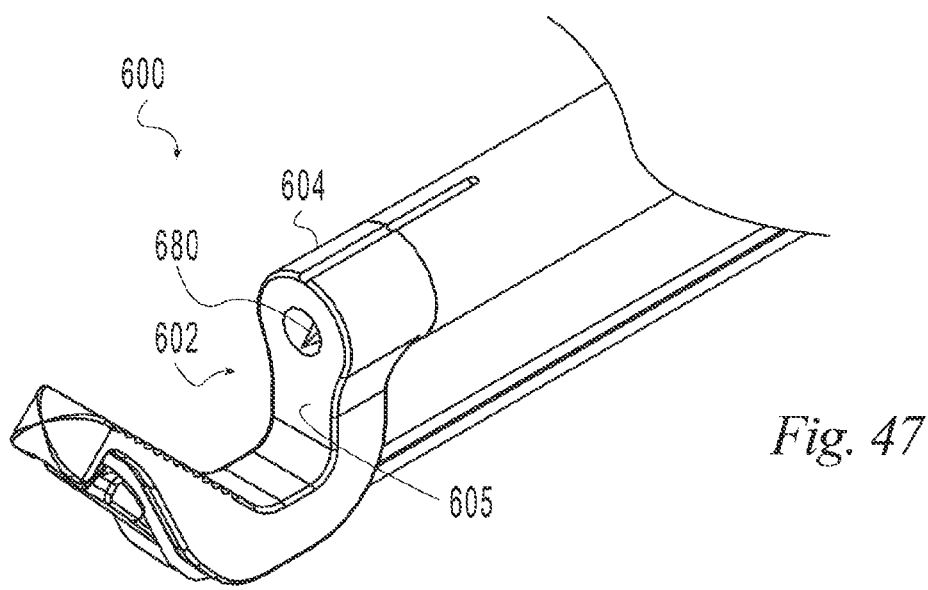
FIG. 47 is a perspective view of an alternative component of the suture passer of FIG. 1 showing an alternative arrangement of the foot and needle.
Figure 48:
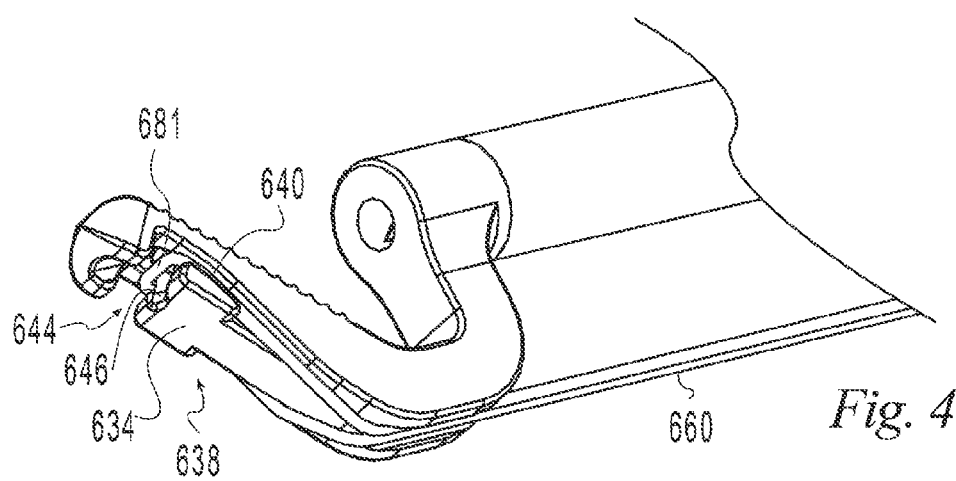
FIG. 48 is a perspective view of the component of FIG. 47 taken from another orientation.

Referring to FIGS. 43 and 44, another alternative to forming stitches with three bights is shown. Here, the second bight 518 has been cut to form third and fourth ends 528, 530. The third and fourth ends 528, 530 are pulled back through the material 510 and then the first and third ends 502, 528 are placed through the first bight 508 to form a first hitch 532 and the second and fourth ends 504, 530 are placed through the third bight 524 to form a second hitch 534.

Alternatively, as shown in FIGS. 45 and 46, the same construct could be produced by forming two bights 508, 518, and cutting through the slack 536 on the back side of the material 510 to produce third and fourth ends 538, 540 which with the first and second ends 502, 504 are used to form hitches 542, 544.

FIGS. 47-56 depict an alternatively configured foot 600 and needle 680 for the suture passer. The foot 600 has a hooked portion defined by a proximal portion 602, an offset portion 610, and a distal portion 612. The proximal portion 602 extends distally from the post 604 along a proximal portion axis 606 diverging from the bore axis 608 at a first angle 609 relative to the bore axis. The first angle 609 is preferably in the range of 25 to 135 degrees; more preferably in the range of 70 to 110 degrees. In the illustrative example of FIGS. 47-56, the first angle 609 is approximately 90 degrees. The offset portion 610 extends distally from the proximal portion 602 at an offset angle 603 relative to the proximal portion axis 606. The offset angle 603 is preferably in the range of 25 to 155 degrees; more preferably in the range of 70 to 110 degrees. In the illustrative example of FIGS. 47-56, the offset angle 603 is approximately 90 degrees. The distal portion 612 extends distally from the offset portion 610 along a distal portion axis 614 converging toward the bore axis 608 at a second angle 616 relative to the bore axis. The second angle 616 is preferably in the range of 0 to 90 degrees; preferably less than 90 degrees; more preferably in the range of 25 to 65 degrees. In the illustrative example of FIGS. 47-56, the second angle 616 is approximately 45 degrees. The offset portion 610 has a length 618 and serves to increase the opening of the hooked portion of the foot 600. The length 618 may be selected to accommodate a particular surgical site. In the illustrative embodiment of FIGS. 47-56, the length is approximately 3 mm and is suited for surgery on the digits of human extremities.

The distal portion 612 of the foot includes a proximal facing surface 620 having first and second opposing lateral borders 622, 624 (FIG. 50) and a distal border 626 at the distal end. The distal portion 612 has a length 628 (FIG. 52) from the distal border to the offset portion 610 and a width 630 between the lateral sides on the proximal facing surface. The distal portion axis 614 extends in the length direction of the distal portion and in the illustrative example of FIGS. 47-56 the length 628 is greater than the width 630. In the illustrative example of FIGS. 47-56, the lateral borders and are parallel to one another. However, it is contemplated that the borders may converge or diverge. The lateral borders 622 and 624 define a foot profile projected parallel to the foot bore axis 608. An opening or eye 632 is formed through the distal portion 612, from the proximal facing surface 620 to a distal facing surface 634, between the lateral borders, and coaxial with the bore axis 608 for receiving the distal end of the needle 680 when the needle 680 is in the second position.

The proximal facing surface 620 defines a proximal facing surface plane that the needle 680 crosses when it is received by the eye 632. The proximal facing surface is textured to reduce the tendency of material, such as soft tissue, to slide on the proximal facing surface 620 as the needle 680 is advanced through material being sutured. The textured surface may include outwardly projecting members such as spikes, ridges, teeth, and other suitable textures. In the illustrative example of FIGS. 47-56, the proximal facing surface 620 includes a plurality of ridges 634 running across the surface in the width direction from lateral border 622 to lateral border 624 separated by grooves 636.

Figure 49:
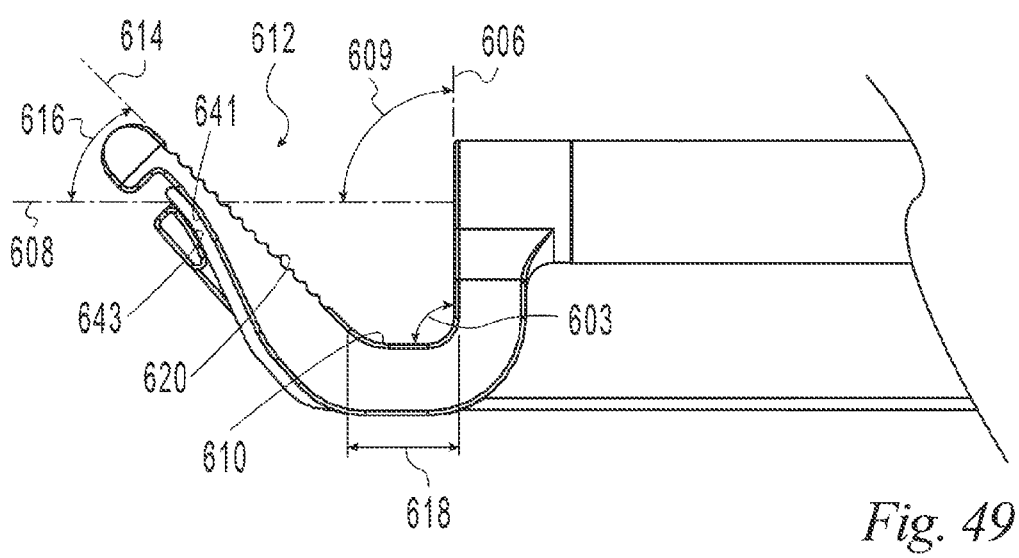
FIG. 49 is a side elevation view of the component of FIG. 47.
Figure 50:
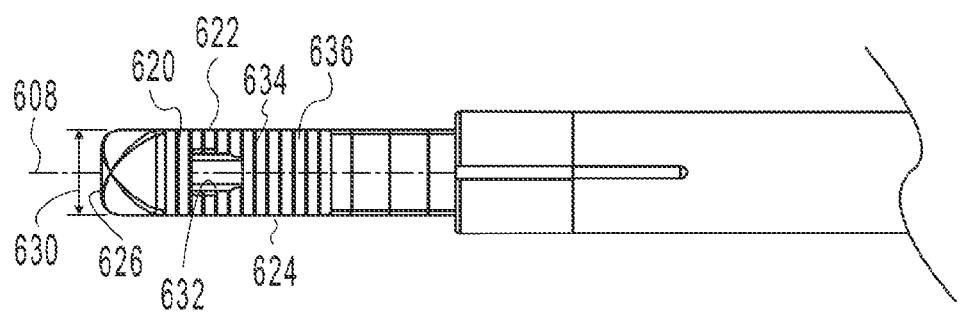
FIG. 50 is a top plan view of the component of FIG. 47.
Figure 51:
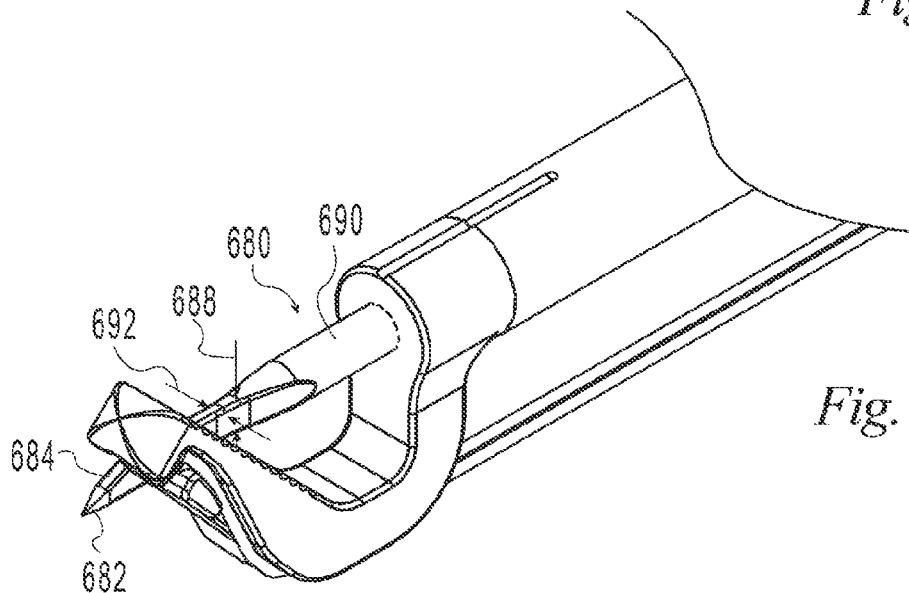
FIG. 51 is a perspective view of the component of FIG. 47 showing a needle in an advanced position.
Figure 52:
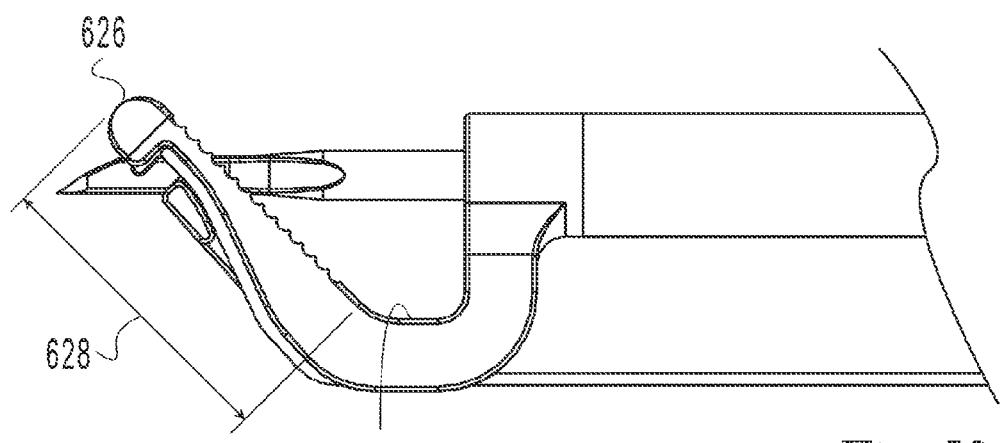
FIG. 52 is a side elevation view of the component of FIG. 47 showing a needle in an advanced position.
Figure 53:
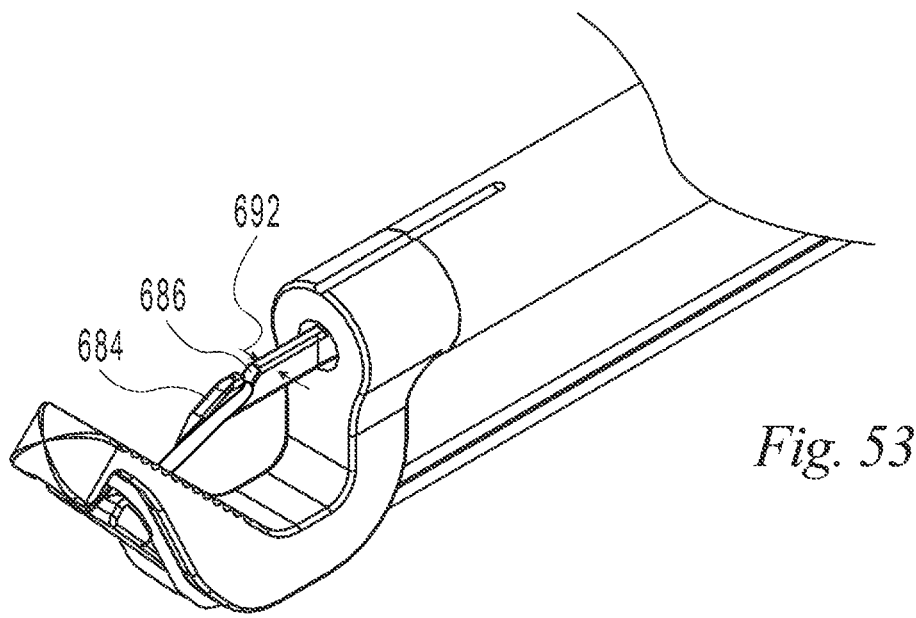
FIG. 53 is a perspective view of the component of FIG. 47 showing the needle partially retracted.
Figure 54:
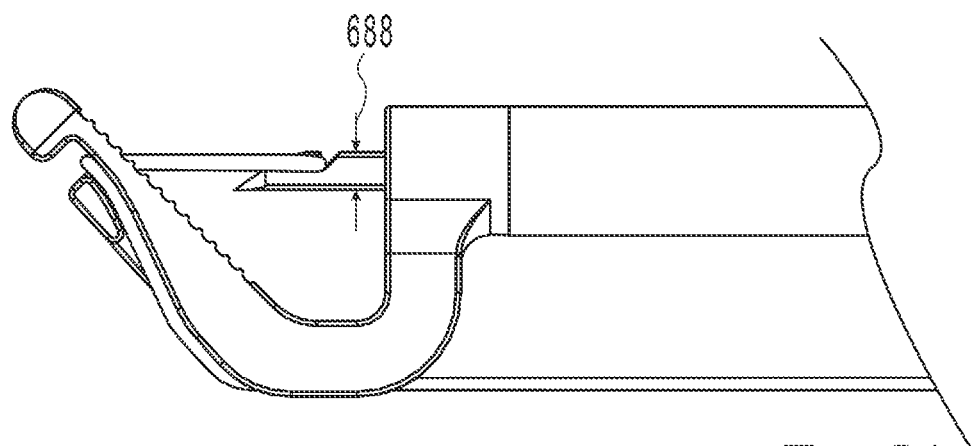
FIG. 54 is a sided elevation view of the component of FIG. 47 showing the needle partially retracted.
Figures 55, 56:
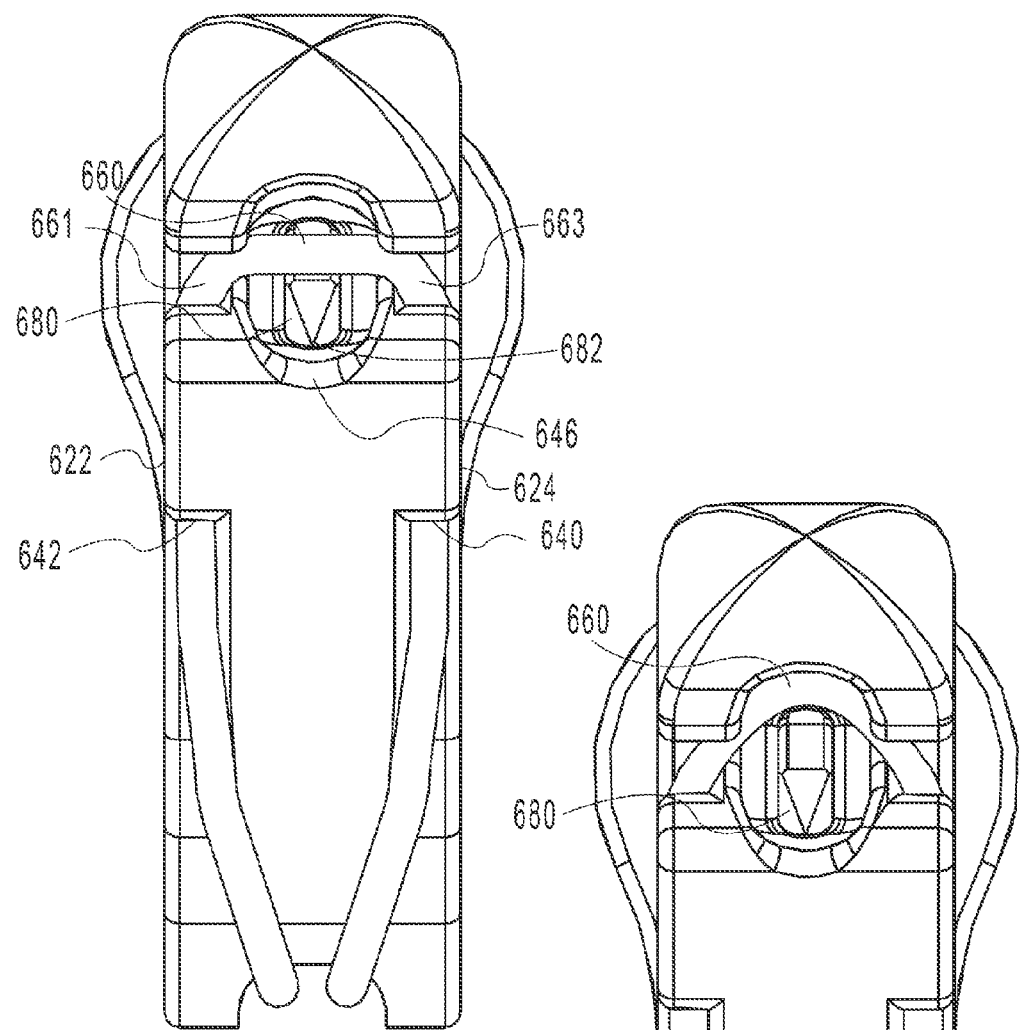
FIG. 55 is a front elevation view of component of FIG. 47 showing the needle partially extended.
FIG. 56 is a front elevation view of component of FIG. 47 showing the needle fully extended.

In the illustrative example of FIGS. 47-56, the suture path does not cross the proximal facing surface 620. The suture path passes around a suture cleat 638 (FIG. 48) defined between the proximal facing surface 620 and distal facing surface 634 by opposed lateral grooves 640 and 642 extending generally in the length direction and connected by a distal groove 644 extending generally in the width direction. The lateral grooves 640 and 642 are recessed into the sides of the distal portion 612. Each lateral groove 640 and 642 is bounded on three sides by the bottom of the groove, an overlying distal facing surface 641 and an underlying proximal facing surface 643 such that the portion of the suture 660 passing through each lateral groove is covered when viewed from a top view looking toward the proximal facing surface and a bottom view looking toward the distal facing surface as seen in FIGS. 50 and 55. The distal groove 644 is recessed into the distal facing surface 634 near the distal end of the foot 600. The distal groove 644 is similarly bounded on three sides. The suture cleat 638 includes a needle groove 646 coaxial with the eye 632. A portion 681 of a suture 660 in the suture path is supported over the needle groove 646. When the needle 680 is advanced, the tip 682 of the needle passes through the needle groove 646 under the suture 660 (FIG. 55). As the needle 680 is further advanced, a bevel 684 on the needle contacts the suture and presses it upwardly and distally (FIG. 56) until the needle notch 686 aligns with the suture 660 and suture tension pulls the suture 660 into the notch 686. As the needle is retracted, it pulls a bight of suture through the eye 632 from the suture path past the proximal facing surface 620.

In the illustrative example of FIGS. 47-56, the suture path includes a first turning point 661 (FIG. 19) and a second turning point 663. The first and second turning points are contained within the foot profile bounded by the first and second lateral borders 622 and 624.

The needle 680 depicted in the illustrative example of FIGS. 47-56 is configured differently from that depicted in the illustrative example of FIGS. 1-12. The needle 680 is rotated so that the bevel 684 and notch 686 (FIG. 51) face upwardly opposite the offset 610 and such that the notch 686 and hook shaped portion of the foot 600 are similarly oriented (FIG. 53) and the height 688 of the needle shank 690 is greater than the width 692. The needle 680 has a sharp distal tip 682 able to cut through material and a blunt edged bevel 684 able to expand an opening cut by the tip 682. In the illustrative example of FIGS. 47-56, the tip 682 is a triangular pyramid with sharp edges. As seen in FIGS. 55 and 56, the suture path and needle 680 are aligned so that the sharp tip 682 clears the suture 660 and the blunt edged bevel 684 contacts the suture and presses it upwardly as the needle 680 advances.

Figure 57:
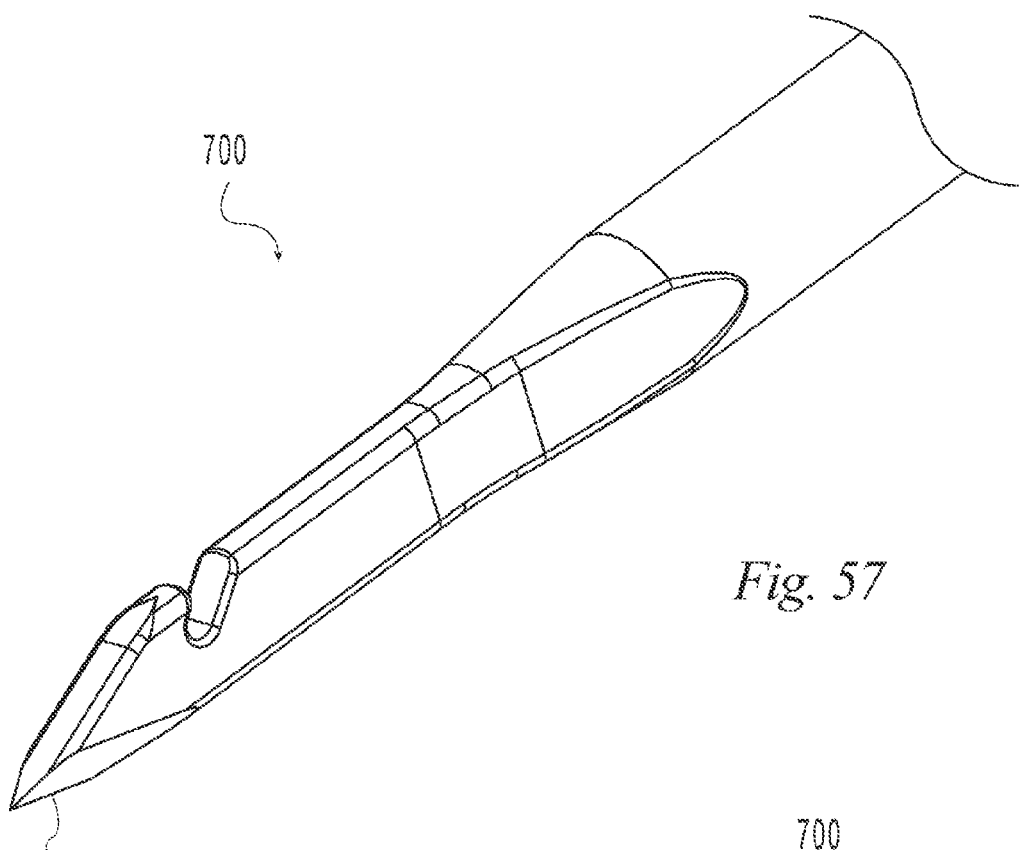
FIG. 57 is a perspective view of an alternative arrangement for the needle.
Figure 58:
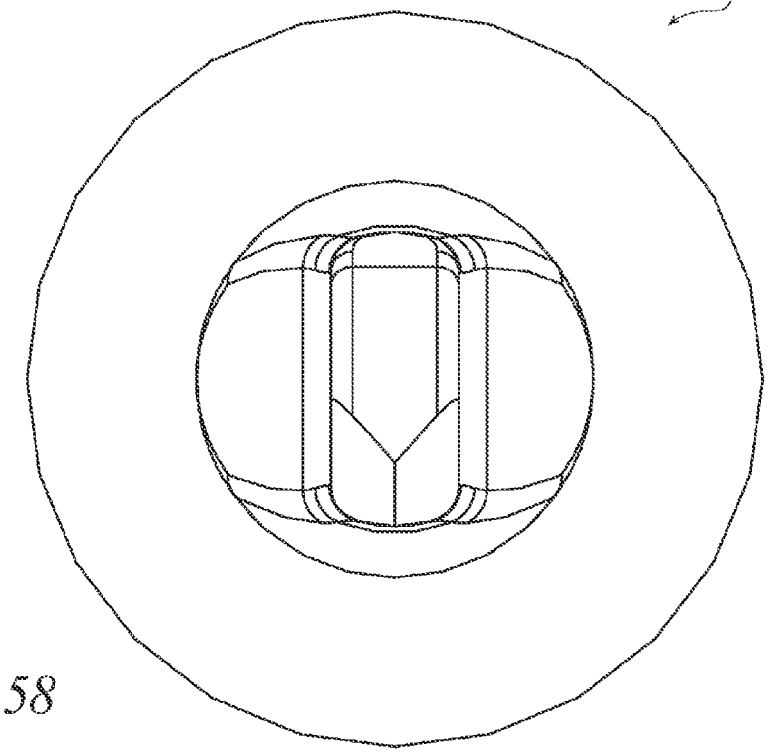
FIG. 58 is a front elevation view of the needle of FIG. 57.

FIGS. 57 and 58 illustrate an alternative needle 700 configuration in which a lower cutting edge 702 of the pyramid extends proximally to provide an elongated cutting edge facing away from the suture to ease needle penetration while protecting the suture.

In the illustrative embodiment of FIGS. 47-56, the suture is contained within the distal portion 612 of the foot. It is contained within the foot profile bounded by the first and second lateral borders 622 and 624 and the distal border 626. Since the suture path does not cross the lateral borders, or side surfaces of the foot, the foot profile remains narrow in the width dimension with a suture loaded. Furthermore, in the illustrative example of FIGS. 47-56, no portion of the suture extends into the interior of the hook defined by the distal facing surface 605 of the proximal portion 602, the offset portion 610, and the proximal facing surface 620 of the distal portion 612 as viewed normal to the hook side plane as seen in FIG. 49. Therefore, there is no suture in the hook to interfere with getting material fully within the hook and there is no impingement of material on the suture that might tend to dislodge suture from the suture path.

In the illustrative example of FIGS. 47-56, the needle is contained within the foot profile bounded by the first and second lateral borders 622 and 624 and the distal border 626. With the needle contained within this profile, the needle does not impinge or snag on material on the sides of the foot 600.

In the illustrative examples of FIGS. 1-12 and 47-56, the suture passer contains no clamping means to secure the material to be sutured while the needle is advanced through the material. In the illustrative example of FIGS. 47-56, the textured proximal facing surface 620 helps to prevent the material from sliding on the surface 620 while the needle is advanced.

Illustrative examples of instruments and methods have been shown in use to pass suture through material to form illustrative hitches. The present invention is not limited to the specific instruments and methods depicted. Furthermore, it is to be understood that instruments and methods according to the present invention may be used to pass any number of bights of suture through one or more materials and form any desirable construct.

What is claimed is:

1. A suture passer comprising:
    a housing defining a motion axis extending proximally to distally;
    a needle mounted for translation along the motion axis between a first proximal position and a second distal position;
    a foot mounted to the housing, the foot having a distal portion with a proximal facing surface, the distal portion including a needle receiving opening in the proximal facing surface aligned with the motion axis and able to receive the needle in the second distal position, the proximal facing surface being defined by a plurality of proximally projecting members, wherein the foot contains no member movable relative to the proximal facing member in opposing clamping relationship to the plurality of projecting members; and
    a suture path including opposed lateral grooves formed into opposed lateral sides of the foot, the suture path extending generally in a length direction and connected by a distal groove extending generally in a width direction that is not the length direction, the distal groove extending from a first of the opposed lateral grooves toward a second of the opposed lateral grooves, each lateral groove being bounded on three sides, wherein the distal portion of the foot further comprises a distal facing surface opposite the proximal facing surface, and wherein each lateral groove is able to receive a suture such that the portion of the suture extending along the suture path is covered when viewed normal to the proximal facing surface.

2. The suture passer of claim 1 wherein the proximally projecting members are ridges separated by grooves.

3. The suture passer of claim 1 wherein the foot further includes a proximal portion with a distal facing surface extending along a proximal portion axis diverging from the motion axis, the proximal portion axis forming a proximal angle relative to the motion axis, the distal portion being connected to the proximal portion, the proximal facing surface of the distal portion extending along a distal portion axis converging distally with the motion axis, the distal portion axis forming a distal angle relative to the motion axis, the distal angle being in the range of 25 to 65 degrees.

4. The suture passer of claim 1 wherein the foot defines a foot side plane in which the foot projects a hook shape having a hook interior, and wherein the suture path is able to receive a suture such that the suture does not extend into the hook interior as viewed normal to the foot side plane.

5. The suture passer of claim 1 wherein the foot includes a proximal portion and an offset portion, and wherein the distal groove extends across at least a portion of the needle receiving opening.

6. The suture passer of claim 5 wherein the offset portion has a length, and the length is manufactured to accommodate a particular surgical site.

7. The suture passer of claim 5 wherein the proximally projecting members are selected from the group consisting of spikes, ridges, and teeth.

8. The suture passer of claim 5 wherein the distal portion has a length and a width, and the length is greater than the width.

9. The suture passer of claim 5 wherein the lateral sides are parallel, converging, or diverging.

10. The suture passer of claim 5 wherein the foot further comprises a suture cleat, and wherein the suture cleat further comprises a needle groove coaxial with the needle receiving opening.

11. The suture passer of claim 5 wherein the proximal portion extends distally from the housing at a first angle relative to the motion axis.

12. The suture passer of claim 11 wherein the first angle is in the range of 70 to 110 degrees.

13. The suture passer of claim 5 wherein the offset portion extends distally from the proximal portion at an offset angle.

14. The suture passer of claim 13 wherein the offset angle is in the range of 70 to 110 degrees.

15. The suture passer of claim 5 wherein the distal portion extends distally from the offset portion along a distal portion axis converging toward the motion axis at a second angle relative to the motion axis.

16. The suture passer of claim 15 wherein the second angle is in the range of 0 to 90 degrees.

17. The suture passer of claim 15 wherein the second angle is in the range of 25 to 65 degrees.

18. The suture passer of claim 5 wherein the proximally projecting members comprise a plurality of ridges running along the width direction.

19. The suture passer of claim 18 wherein the plurality of ridges are separated by grooves.

* * * * *